(12) United States Patent
Stone et al.

(10) Patent No.: US 10,512,427 B2
(45) Date of Patent: Dec. 24, 2019

(54) BLADDER FULLNESS LEVEL INDICATION BASED ON BLADDER OSCILLATION FREQUENCY

(71) Applicant: Medtronic, Inc., Minneapolis, MN (US)

(72) Inventors: Richard T. Stone, Minneapolis, MN (US); Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 1725 days.

(21) Appl. No.: 13/764,911

(22) Filed: Feb. 12, 2013

(65) Prior Publication Data

US 2013/0289446 A1 Oct. 31, 2013

Related U.S. Application Data

(60) Provisional application No. 61/639,218, filed on Apr. 27, 2012.

(51) Int. Cl.
*A61B 7/00* (2006.01)
*A61B 5/20* (2006.01)
(Continued)

(52) U.S. Cl.
CPC ............ *A61B 5/204* (2013.01); *A61B 5/0002* (2013.01); *A61B 5/11* (2013.01); *A61B 5/4836* (2013.01); *A61B 5/686* (2013.01); *A61B 5/725* (2013.01); *A61B 5/7278* (2013.01); *A61B 5/742* (2013.01); *A61B 5/7405* (2013.01); *A61B 5/746* (2013.01); *A61B 5/7455* (2013.01); *A61B 5/7475* (2013.01); *A61B 7/00* (2013.01); *A61N 1/0521* (2013.01); *A61N 1/36007* (2013.01)

(58) Field of Classification Search
CPC .............. A61B 7/003; A61B 7/04; A61B 7/00
USPC ........................................................ 600/586
See application file for complete search history.

(56) References Cited

U.S. PATENT DOCUMENTS 6,836,684 B1  12/2004  Rijkhoff et al.
6,896,651 B2   5/2005  Gross et al.
(Continued)

FOREIGN PATENT DOCUMENTS

WO   WO2000/019940   4/2000
WO   WO2010/111321   9/2010

*Primary Examiner* — Daniel L Cerioni
(74) *Attorney, Agent, or Firm* — Shumaker & Sieffert, P.A.

(57) ABSTRACT

A bladder fullness level of a patient may be determined based on a frequency of mechanical oscillations of the bladder of the patient. The bladder may mechanically oscillate in response to the occurrence of non-micturition contractions of the bladder of the patient, which are contractions not associated with urine release. The frequency at which the bladder oscillates, e.g., following a non-micturition contraction, may have a correlation to the bladder fullness level. In some examples, a medical device may be configured to control the delivery of electrical stimulation therapy to the patient based on the oscillation frequency of the bladder. In addition, or instead to controlling therapy based on the oscillation frequency of the bladder, a notification, such as a patient or patient caretaker notification, may be generated (e.g., automatically by a processor of a device) based on the oscillation frequency of the bladder.

65 Claims, 9 Drawing Sheets

(51) Int. Cl.
*A61B 5/11* (2006.01)
*A61B 5/00* (2006.01)
*A61N 1/36* (2006.01)
*A61N 1/05* (2006.01)

(56) References Cited

U.S. PATENT DOCUMENTS

| | | |
|---|---|---|
| 7,415,308 B2 | 8/2008 | Gerber et al. |
| 7,769,460 B2 | 8/2010 | Gerber |
| 7,930,034 B2 | 4/2011 | Gerber |
| 2004/0249293 A1* | 12/2004 | Sandler ............... A61B 7/00 600/481 |
| 2006/0020225 A1* | 1/2006 | Gerber ............... A61B 5/14539 600/561 |
| 2006/0190051 A1* | 8/2006 | Gerber ............... A61N 1/36007 607/41 |
| 2007/0027494 A1* | 2/2007 | Gerber ............... A61B 5/204 607/41 |
| 2007/0027495 A1 | 2/2007 | Gerber |
| 2007/0100387 A1 | 5/2007 | Gerber |
| 2007/0100388 A1* | 5/2007 | Gerber ............... A61N 1/36007 607/41 |
| 2007/0123778 A1* | 5/2007 | Kantorovich ......... A61B 5/204 600/437 |
| 2008/0300449 A1* | 12/2008 | Gerber ............... A61N 1/36007 600/30 |
| 2008/0300470 A1* | 12/2008 | Gerber ............... A61B 5/1116 600/301 |
| 2011/0015704 A1* | 1/2011 | Ternes ............... A61B 5/024 607/62 |
| 2012/0101326 A1* | 4/2012 | Simon ............... A61N 1/36007 600/9 |
| 2013/0310706 A1* | 11/2013 | Stone ............... A61B 8/56 600/561 |

* cited by examiner

BLADDER FULLNESS LEVEL INDICATION BASED ON BLADDER OSCILLATION FREQUENCY

TECHNICAL FIELD

The disclosure relates to implantable medical devices and, more particularly, medical devices that sense a physiological parameter of a patient.

BACKGROUND

Lower urinary tract dysfunction, such as an inability to control urinary function, may afflict people of all ages, genders, and races. Various muscles, nerves, organs and conduits within the urinary tract cooperate to collect, store and release urine. A variety of patient conditions may compromise urinary tract performance and contribute to incontinence. Many of the disorders may be associated with nerve damage due to pregnancy and vaginal childbirth, aging, or illness. Example lower urinary tract dysfunctions include, for example, urgency and frequency disorders, urge incontinence, stress incontinence, and urinary retention disorders. Urgency and frequency disorders may involve the feeling of impending urination without the actual voiding of urine. Retention and voiding dysfunctions, for example, may involve the loss of urine and be at least partially attributable to injury or disease (e.g., a spinal cord injury). Some patients suffering from injury or disease that affects bladder function may not be able to void or have reduced levels of sensation when the bladder is full. These conditions may result in kidney damage and other complications.

SUMMARY

A bladder fullness level of a patient may be indicated by an oscillation frequency of the bladder of the patient. The bladder may mechanically oscillate in response to the occurrence of non-micturition contractions of the bladder, which are contractions not associated with urine release. The frequency at which the bladder oscillates, e.g., following a non-micturition contraction, may be correlated to the bladder fullness level. It is believed that the oscillation frequency of the bladder decreases with bladder fullness.

In some examples, a sensor configured to generate a signal indicative of the oscillation frequency of the bladder is implanted in the patient. Devices, systems, and techniques for taking an action based on an oscillation frequency of the bladder determined based on the signal from the sensor are described.

In some examples, a determined oscillation frequency of the bladder may be used to control therapy delivery to the patient. For example, a medical device (implantable or external) may be configured to control the delivery of electrical stimulation therapy to the patient based on the determined oscillation frequency of the bladder, where the electrical stimulation therapy is configured to manage urinary incontinence. As an example, the medical device may initiate therapy delivery to the patient in response to detecting an oscillation frequency of the bladder that is less than or equal to a threshold frequency value. As another example, the medical device may adjust therapy deliver to the patient (e.g., to provide an additional "boost" of therapy) in response to detecting an oscillation frequency of the bladder that is less than or equal to a threshold frequency value in order to help prevent the occurrence of an involuntary voiding event.

In addition, or instead of controlling therapy based on the oscillation frequency of the bladder, a notification may be generated (e.g., automatically by a processor of a device) upon detecting an oscillation frequency less than or equal to a threshold bladder fullness level. The notification may indicate an elevated bladder fullness level, such as a level at which voiding is desired. The notification may alert the patient or patient caretaker that voiding is advisable.

In one example, the disclosure is directed to a system comprising, a sensor configured to generate a signal indicative of mechanical oscillation of a bladder of a patient, and a processor configured to receive the signal from the sensor, determine an oscillation frequency of the bladder based on the signal, and take a responsive action based on the oscillation frequency.

In another example, the disclosure is directed to a method comprising, with a processor, receiving, from a sensor, a signal indicative of mechanical oscillations of a bladder of a patient, with the processor, determining an oscillation frequency of the bladder based on the signal, with the processor, and, with the processor, taking a responsive action based on the oscillation frequency.

In another example, the disclosure is directed to a system comprising means for receiving, from a sensor, a signal indicative of mechanical oscillations of a bladder of a patient, means for determining an oscillation frequency of the bladder based on the signal, and means for taking a responsive action based on the oscillation frequency.

In another example, the disclosure is directed to a computer-readable medium comprising instructions. When executed by a processor, the instructions cause the processor to receive, from a sensor, a signal indicative of mechanical oscillations of a bladder of a patient, determine an oscillation frequency of the bladder based on the signal, and take a responsive action based on the oscillation frequency.

In another example, the disclosure is directed to a system comprising a sensor configured to generate a signal indicative of mechanical oscillation of a bladder of a patient, and a processor configured to receive the signal from the sensor, determine an oscillation frequency of the bladder based on the signal, determine, based on the oscillation frequency of the bladder, a function that indicates the change in volume of the bladder of the patient per unit time, and determine a current bladder volume based on the function.

In another example, the disclosure is directed to a method comprising with a processor, receiving, from a sensor, a signal indicative of mechanical oscillations of a bladder of a patient, with the processor, determining an oscillation frequency of the bladder based on the signal, with the processor, determining, based on the oscillation frequency of the bladder, a function that indicates the change in volume of the bladder of the patient per unit time, with the processor, determining a current bladder volume based on the function, and, with the processor, taking a responsive action based on the current bladder volume.

In another example, the disclosure is directed to a system comprising means for receiving, from a sensor, a signal indicative of mechanical oscillations of a bladder of a patient, means for determining an oscillation frequency of the bladder based on the signal, means for determining, based on the oscillation frequency of the bladder, a function that indicates the change in volume of the bladder of the patient per unit time, means for determining a current bladder volume based on the function, and means for taking a responsive action based on the current bladder volume.

In another example, the disclosure is directed to a computer-readable medium comprising instructions. When executed by a processor, the instructions cause the processor to receive, from a sensor, a signal indicative of mechanical oscillations of a bladder of a patient, determine an oscillation frequency of the bladder based on the signal, determine, based on the oscillation frequency of the bladder, a function that indicates the change in volume of the bladder of the patient per unit time, determine a current bladder volume based on the function, and take a responsive action based on the current bladder volume.

In another aspect, the disclosure is directed to a computer-readable storage medium, which may be a non-transitory article of manufacture. The computer-readable storage medium includes computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein.

The details of one or more examples are set forth in the accompanying drawings and the description below. Other features, objects, and advantages will be apparent from the description and drawings, and from the claims.

DETAILED DESCRIPTION

Figure 1:
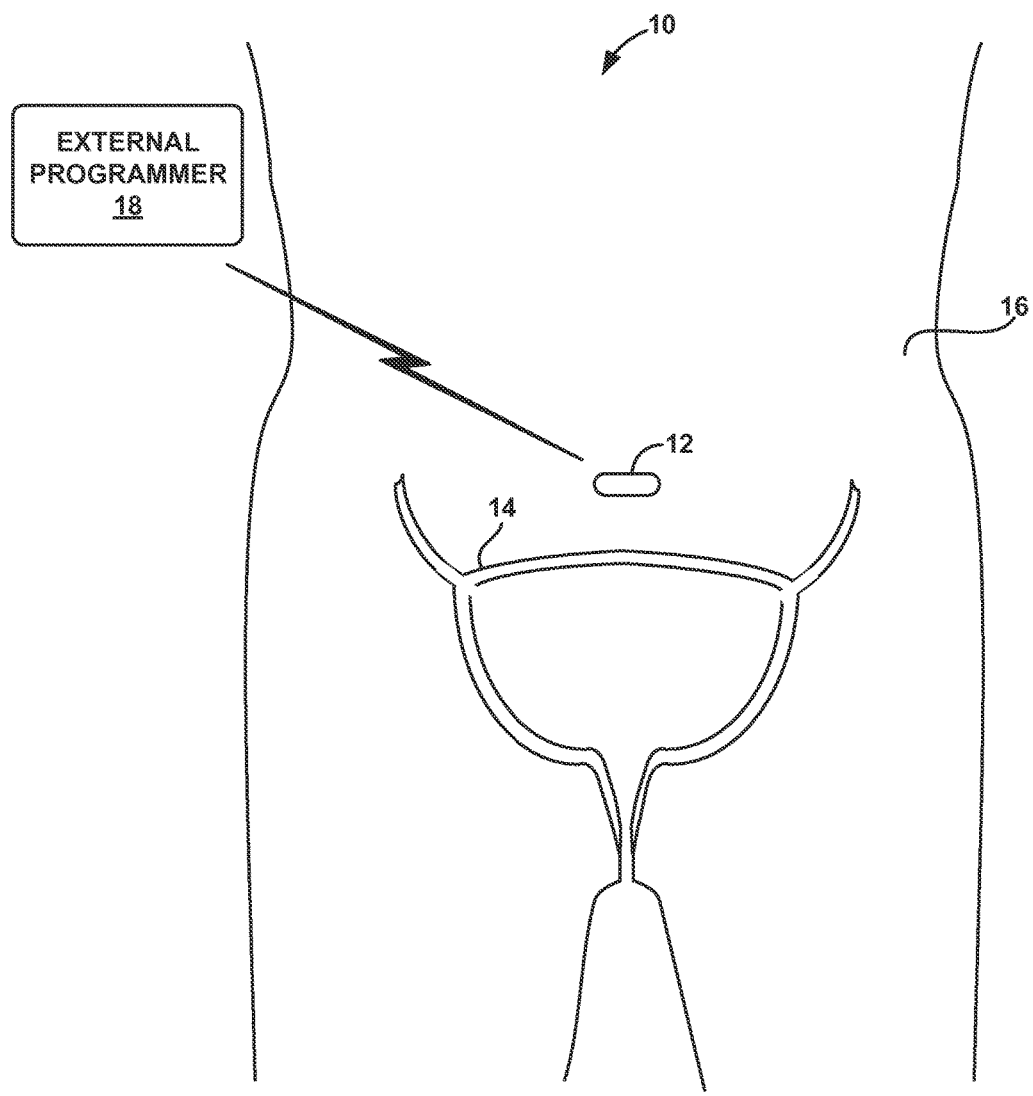
FIG. 1 is a conceptual diagram of an example system that includes a sensor configured to sense mechanical oscillations of a bladder of a patient.

A frequency of the mechanical oscillations of a bladder of a patient may be indicative of a bladder fullness level of a patient. The bladder (e.g., a wall of the bladder) may mechanically oscillate in response to the occurrence of non-micturition contractions of the bladder of the patient. A non-micturition contraction is a phasic contraction of a bladder not associated with urine release and differs from bladder contractions (also referred to as "micturition contractions") that occur as part of urine release. The bladder oscillations may be caused from the occurrence of the non-micturition contractions of the bladder.

The fundamental frequency of the oscillations may be driven by the mass of the bladder, which is at least partially a function of the volume of urine in the bladder. Thus, the frequency (also interchangeably referred to herein as an "oscillation frequency" and a "ringing frequency") at which the bladder mechanically oscillates, e.g., following a non-micturition contraction, may correlate to the bladder fullness level. It is believed that the oscillation frequency of the bladder decreases as the bladder volume increases. In this way, the oscillation frequency of the bladder may be an indicator of bladder fullness level of a patient.

As discussed in further detail below, one or more responsive actions may be taken in response to detecting a particular oscillation frequency of a bladder of a patient, which may indicate a particular bladder fullness level of the patient. In some examples, the oscillation frequency may be used to control the delivery of therapy to the patient to manage a lower urinary tract dysfunction of the patient. In addition, or instead of controlling therapy based on the oscillation frequency of the bladder, a notification (e.g., to the patient or patient caretaker) may be generated based on the oscillation frequency.

The oscillation frequency of the bladder may indicate a bladder fullness level of a patient, regardless of whether the patient has an overactive bladder or a normal bladder, e.g., a bladder not impaired by a lower urinary tract dysfunction, because the mechanical oscillation frequency of the bladder appears to be a function of the mass of the bladder (e.g., the amount of urine contained in the bladder), the curvature of the walls of the bladder and the tension of the bladder wall.

Some patient disorders may cause or otherwise be associated with dysfunctions of the lower urinary tract. Example dysfunctions of the lower urinary tract include improper functioning of the bladder or urinary tract, and may include, for example, an overactive bladder, urgency, urine retention disorder, or urinary incontinence. Urgency is a sudden, compelling urge to urinate, and may, though not always, be associated with urinary incontinence. Urinary incontinence refers to a condition of in which involuntary voiding events may occur (i.e., involuntary loss of urine), and may include urge incontinence, stress incontinence, or both stress and urge incontinence, which may be referred to as mixed urinary incontinence. Symptoms of overactive bladder may include urgency, frequent urination, or both.

One type of therapy that has been proposed for managing lower urinary tract dysfunction (e.g., to minimize bladder contractions, urgency, the number of involuntary voiding events, or any combination thereof) includes delivery of electrical stimulation to a target tissue site within a patient. For example, delivery of electrical stimulation from a medical device to a target tissue site proximate any one or more of a spinal nerve, a sacral nerve, a pudendal nerve, dorsal genital nerve (e.g., the dorsal nerve of the penis or clitoris), an inferior rectal nerve, a perineal nerve, a nerve tract of the leg (e.g., sciatic nerve, peroneal nerve or tibial nerve) or branches of any of the aforementioned nerves to modulate the nerve activities may provide an effective therapy for managing lower urinary tract dysfunction. As an example, electrical stimulation to modulate the activity of the sacral nerve, the dorsal-genital nerve, and/or the pudendal nerve (or branches of these nerves) may help reduce bladder contraction frequency, which can mitigate urgency. A determined oscillation frequency of the bladder may be used to control the timing of lower urinary tract dysfunction therapy delivery to the patient or to adjust a stimulation parameter value of lower urinary tract dysfunction therapy that is currently being delivered to the patient (e.g., stimulation parameter values of therapy that was actively being delivered to the patient at the time the oscillation frequency was determined).

In other examples, the oscillation frequency of the bladder may be used to time the generation of a notification to the patient or a patient caretaker. The notification may indicate an elevated bladder fullness level, such as a level at which voiding is advisable. Some patients suffering from injury or disease that affects bladder function may not be able to voluntarily void or may have reduced levels of sensation when the bladder is full, or may need the assistance of a catheter to void. The bladder fullness level notification may be used to notify the patient when a bladder fullness reaches a level at which voiding is advisable, or, if the patient is unable to void without catheterization, the notification may be used to notify a patient caretaker that the patient should be catheterized.

In some examples, one or more past sensed oscillation frequencies of the bladder may be used to predict a bladder fullness level of a patient at some point in time, which may be in the future relative to the time at which the one or more oscillation frequencies of the bladder is sensed. The urine production rate of a patient may be relatively slowly changing except after large amounts of liquid (e.g., water) is ingested. Thus, a bladder fill rate of the patient may be indicated by a volume prediction function (linear or nonlinear) that is based on a plurality of determined bladder oscillation frequencies over time. A bladder oscillation frequency determination at a particular point in time may be used to update a predicted bladder fill level. In some examples, a fading set of change in volume per change in time ($\Delta V/\Delta t$) measurements may be used to determine the rate of change of volume. Recorded times with urine volumes within the bladder since micturition can be used to assess rate of urine production. Temporal rates of urine production along with urine volumes within the bladder can be used to produce a urine volume within the bladder or a bladder volume function in time. This function may be useful for determining the bladder fullness level between mechanical oscillation measurement events.

Each new volume measurement and associated bladder oscillation frequency determination may be used to update the volume prediction function. The real time fullness predictor may not be dependent upon the numerical details of the measurement technique. In some examples, any of the responsive actions described above may then be taken based on a predicted bladder fullness level of a patient determined based on the current and previously measured bladder oscillation frequencies.

FIG. 1 is a conceptual diagram that illustrates an example system 10 that includes sensor 12 configured to sense mechanical oscillations bladder 14 of patient 16, where the mechanical oscillations may be caused by non-micturition contractions of bladder 14. Sensor 12 is configured to generate a signal that changes as a function of the mechanical oscillations of bladder 14. Sensor 12 may include, for example, an acoustic or pressure sensor, a flexible printed circuit comprising pressure sensitive ink, a piezoresistor, a piezoelectric crystal, a capacitive sensor, a load cell, a force sensor, a displacement sensor or another type of analog resistance or voltage based sensor.

Sensor 12 may be implanted at any suitable location in patient 16 and relatively close to bladder 14, e.g., such that as bladder 14 moves during the mechanical oscillations, sensor 12 itself or a sensing element of sensor 12 moves or so that sensor 12 may sense an electrical parameter of patient 16 that changes as a function of the mechanical oscillations. Sensor 12 may then generate an electrical signal changes as a function of this movement or electrical activity, which may correspond to the mechanical oscillations of bladder 14. In some examples, sensor 12 may be implanted under an abdominal muscle of patient 16. Instead, or in addition, in some examples, sensor 12 is implanted behind the pubic bone of patient 16, which may function to shield sensor 12 from intestinal contractions while providing relatively close placement to bladder 14. Shielding sensor 12 from intestinal contractions may help reduce the amount of noise in the signal generated by sensor 12 that is attributable to the intestinal contractions.

System 10 also includes external device 18, which, in the example shown in FIG. 1, is configured to communicate with sensor 12. In some examples, external device 18 is configured to receive signals generated by sensor 12, where the signals are indicative of mechanical oscillation of bladder 14. The signal transmitted by sensor 12 and received by external device 18 can be, for example, the raw signal generated by sensor 12, a signal to which sensor 12 has already applied a filter (e.g., a band pass filter, a low-pass filter, or a high-pass filter), or any other signal that indicates the frequency of the mechanical oscillation of bladder 14.

In some examples, external device 18 is configured to receive the signal generated by sensor 12, and determine the oscillation frequency of bladder 14 based on the signal. For example, external device 18 may include a processor that determines the fundamental frequency of the signal from sensor 12. In contrast to situations in which a parameter of patient 16 is determined based on relatively small changes in a characteristic of the sensor signal, with system 10, the number and types of suitable sensors 12 may be increased and the cost of suitable sensors 12 may be relatively low because it is the fundamental frequency of the signal from sensor 12 that is of interest for determining the oscillation frequency of bladder 14.

In addition to or instead of external device 18 determining the oscillation frequency of bladder 14, in some examples, sensor 12 includes a processor that is configured to determine the oscillation frequency of bladder 14 based on the signal generated by sensor 12 that changes as a function of mechanical oscillation of bladder 14. Sensor 12 may transmit the determined oscillation frequency to external device 18 in some examples.

In some examples, external device 18 is configured to generate a notification based on the oscillation frequency (determined by sensor, external device 18, or any other device of system 10). For example, external device 18 may generate a notification in response to determining the determined oscillation frequency of bladder 14 is less than or equal to a predetermined threshold value. The predetermined threshold value may be stored by external device 18, sensor 12, or another device, which may be co-located with system 10 or may be remotely located from system 10 and in communication with system 10 via a communication link (e.g., via a telephone link or via the internet). As discussed above, the notification may indicate an elevated bladder fullness level, such as a level at which voiding is advisable.

In response to receiving the notification, patient 16 may void or, if patient 16 is unable to void without catheterization, a patient caretaker may catheterize patient 16 or otherwise assist patient 16 with voiding to reduce the fill level of bladder 14.

External device 18 may be configured to provide a notification using any suitable technique. In some examples, external device 18 may be configured to display a visible message, emit an audible alert signal or provide a somatosensory alert (e.g., by causing a housing of external device 18 to vibrate in a particular pattern or to just vibrate continuously for a period of time) in order to provide the notification, or any combination of the aforementioned types of notifications.

In some examples, the notification is provided by sensor 12, rather than external device 18. In some of these examples, system 10 may not include external device 18. Sensor 12 may generate a notification based on the determined oscillation frequency using any suitable technique. In one example, sensor 12 may generate the alert by generating a somatosensory alert, such as by vibrating in a manner that patient 16 recognizes as the notification.

As discussed above, in some examples, a system that includes sensor 12 configured to generate a signal indicative of oscillations of bladder 14 may also include a medical device that is configured to deliver therapy to patient 16, e.g., to manage a lower urinary tract dysfunction. The medical device may be implantable or external.

Figure 2:
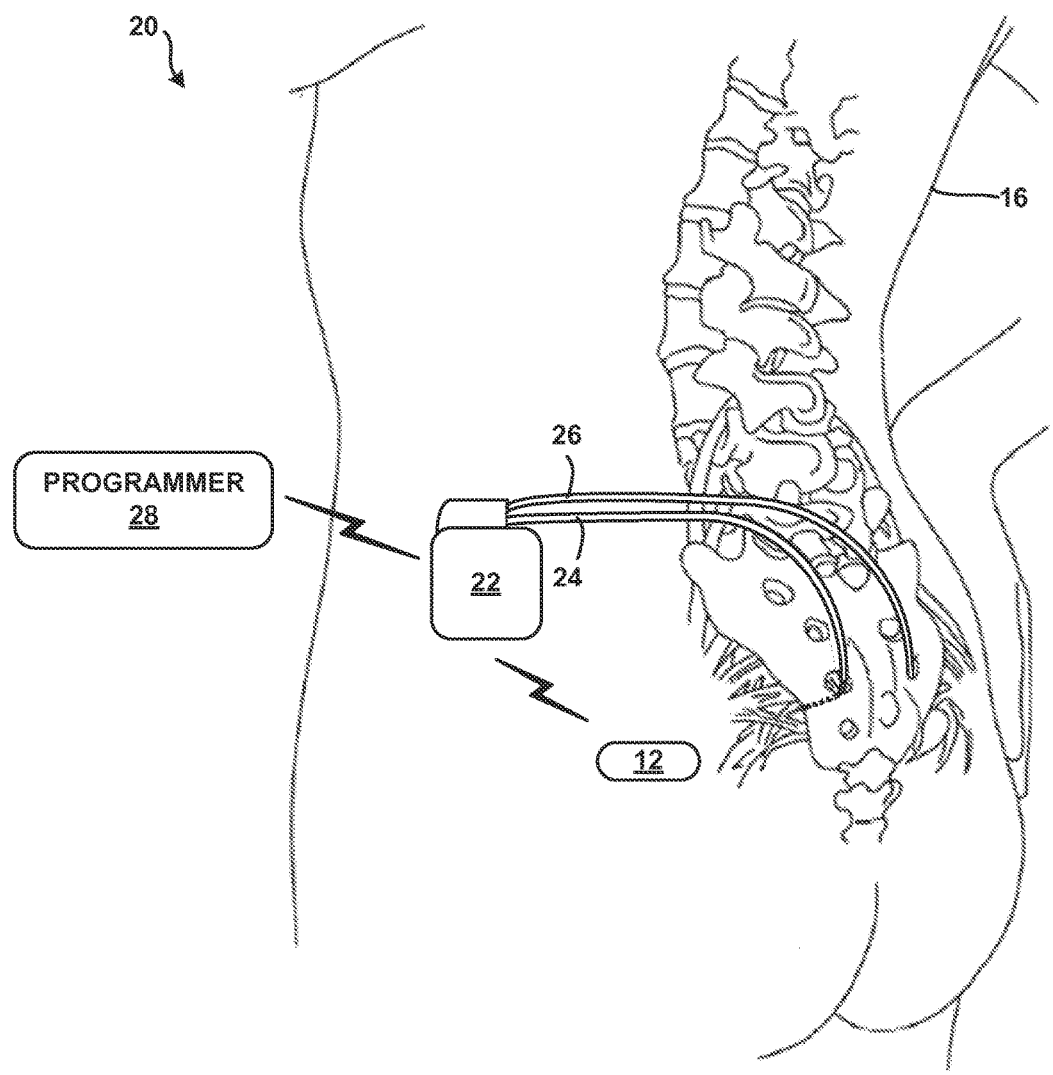
FIG. 2 is a conceptual diagram of an example therapy system that includes a sensor configured to sense mechanical oscillations of a bladder of a patient and an implantable medical device (IMD) configured to deliver therapy to the patient to manage a lower urinary tract dysfunction.

FIG. 2 is a conceptual diagram of an example therapy system 20 that includes sensor 12 configured to sense mechanical oscillations of bladder 14 (not shown in FIG. 2) of patient 16 and IMD 22 configured to deliver therapy to patient 16 to manage a lower urinary tract dysfunction. In the example shown in FIG. 2, IMD 22 is coupled to leads 24, 26. System 10 also includes an external programmer 28, which may have function similar or identical to that of external device 18 (FIG. 1), and, in addition, may be configured to communicate with IMD 22 via a wireless communication protocol.

Sensor 12 and IMD 22 may be configured to communicate with each other via a wireless communication protocol. For example, sensor 12 may be configured to transmit a signal indicative of sensed bladder oscillations of patient 16 to IMD 22. Sensor 12 may transmit to IMD 22 a raw signal generated by sensor 12, a signal to which sensor 12 has already applied a filter (e.g., a band pass filter, a low-pass filter, or a high-pass filter), or any other signal that indicates the frequency of the mechanical oscillation of bladder 14. In other examples, sensor 22 determines the oscillation frequency of bladder 14 and transmits the determined oscillation frequency to IMD 22.

IMD 22 is configured to operate as a therapy device that delivers electrical stimulation therapy to patient 16 by generating and delivering a programmable electrical stimulation signal (e.g., in the form of electrical pulses or a continuous waveform) to one or more target therapy sites proximate electrodes of leads 24, 26. In the example shown in FIG. 2, the electrodes of each lead 24, 26 are disposed proximate to a distal end of the respective lead 24, 26. The target therapy sites may be selected to modulate activity of, for example, a pelvic floor nerve, a pelvic floor muscle, the urinary sphincter, the anal sphincter, other pelvic floor targets, or other nerves that make up the neural network involved in the lower urinary tract function of patient 16. Pelvic floor nerves include peripheral nerves such as sacral nerves, pudendal nerves and associated branches, and dorsal genital nerves. Examples of nerves in the neural network involved in lower urinary tract function include spinal nerves, a sacral nerve, a pudendal nerve, dorsal genital nerve, a tibial nerve, an inferior rectal nerve, a perineal nerve, or branches of any of the aforementioned nerves.

In some examples, the target tissue sites can be identified prior to implantation of leads 24, 26. For example, a device, such as an introducer or needle, can be introduced into patient 16 and a test electrical signal can be delivered to tissue of patient 16 via the device.

The device may be moved within patient 16 until a desirable physiological response is elicited by the test electrical signal, which can indicate that the device (e.g., the one or more electrodes used to deliver the test stimulation) is positioned at a tissue site that captures a target nerve. In some examples, the physiological response may be detected through a motor response that may be visually detected, a sensory response as reported by patient 16, or through an electrical response (e.g., sensed nerve signals). Electrodes of leads 24, 26 can subsequently be positioned at the tissue site at which the test electrical signal elicited the desirable physiological response. In other examples, the test stimulation may be delivered via leads 24, 26.

In some examples, IMD 22 may be surgically implanted in patient 16 at any suitable location within patient 16, such as in the side of the lower abdomen or the side of the lower back or upper buttocks. IMD 22 can include a biocompatible outer housing, which may be formed from titanium, stainless steel, a liquid crystal polymer, or the like. One or more medical leads, e.g., leads 24, 26, may be connected to IMD 22 and surgically or percutaneously tunneled to place one or more electrodes of the respective lead at a target tissue site proximate to a desired nerve or muscle, e.g., one of the previously listed target therapy sites, such as a tissue site proximate a spinal, sacral or pudendal nerve. The proximal ends of leads 24, 26 are both electrically and mechanically coupled to IMD 22 either directly or indirectly, e.g., via respective lead extensions.

Electrical conductors disposed within the lead bodies of leads 24, 26 electrically connect electrodes of the respective lead to a therapy delivery module (e.g., a stimulation generator) of IMD 22. In addition, in some examples, IMD 22 includes a sensing module and the electrical conductors of leads 24, 26 electrically connect the electrodes of the respective lead to a sensing module of IMD 22, which enables IMD 22 to sense a physiological parameter of patient 16 via the electrodes. Example physiological parameters that may be sensed via electrodes of leads 24, 26 include, but are not limited to, any one or more of electrical nerve activity, bladder impedance, electrical cardiac signals, and muscle activity (e.g., via an electromyogram (EMG)). In addition, in some examples, sensor 12 may be a part of IMD 22 and may be enclosed in the same housing as the therapy delivery module of IMD 22, rather than being in physically separate housings as shown in the example of FIG. 2.

Leads 24, 26 can be positioned to deliver electrical stimulation to target tissue sites proximate branches of the same nerve or branches of different nerves. For example, IMD 22 can deliver bilateral stimulation to patient 16 by delivering electrical stimulation to both the left and right nerve branches (or portions) of the same nerve and/or by delivering electrical stimulation to a left branch of a first nerve and a right branch of a second nerve that is different than the first nerve. As an example, leads 24, 26 can be positioned to deliver electrical stimulation to tissue sites on both lateral sides of patient 16 to modulate activity of both a left and a right dorsal genital nerve or nerve portion, both a left and a right pudendal nerve or nerve portion, and/or both a dorsal genital nerve or nerve portion and a pudendal nerve or nerve portion on different lateral sides of patient 16.

In some examples, IMD 22 is configured to deliver electrical stimulation therapy to patient 16 to generate a physiological response that elicits an inhibitory physiological response related to voiding (e.g., reduces a bladder contraction frequency or other symptoms of urgency) in an open-loop manner without intervention from a user or a sensor. For example, IMD 22 may deliver electrical stimulation therapy to patient 16 according to a predetermined schedule or substantially continuously.

In other examples, IMD 22 may deliver the electrical stimulation therapy to patient 16 in a closed-loop manner or a pseudo-closed-loop manner. For example, as discussed with respect to FIG. 8, IMD 22 may be configured to initiate the delivery of electrical stimulation therapy to patient 16 in response to detecting a oscillation frequency of bladder 14 that is less than or equal to a predetermined threshold value (which may be stored by IMD 22, programmer 18, sensor 12, or another device). As another example, as discussed with respect to FIG. 9, IMD 22 may be configured to deliver electrical stimulation therapy to patient 16 and, in response to detecting a oscillation frequency of bladder 14 that is less than or equal to a predetermined threshold value, adjust at least one stimulation parameter value of the therapy that was delivered to patient 16 at the time the oscillation frequency was detected or occurred. The adjustment to the stimulation therapy may increase the intensity of the electrical stimulation therapy (which may be a function of one or more stimulation parameter values, such as current amplitude, voltage amplitude, frequency, and, in the case of stimulation pulses, pulse width).

Figure 10:
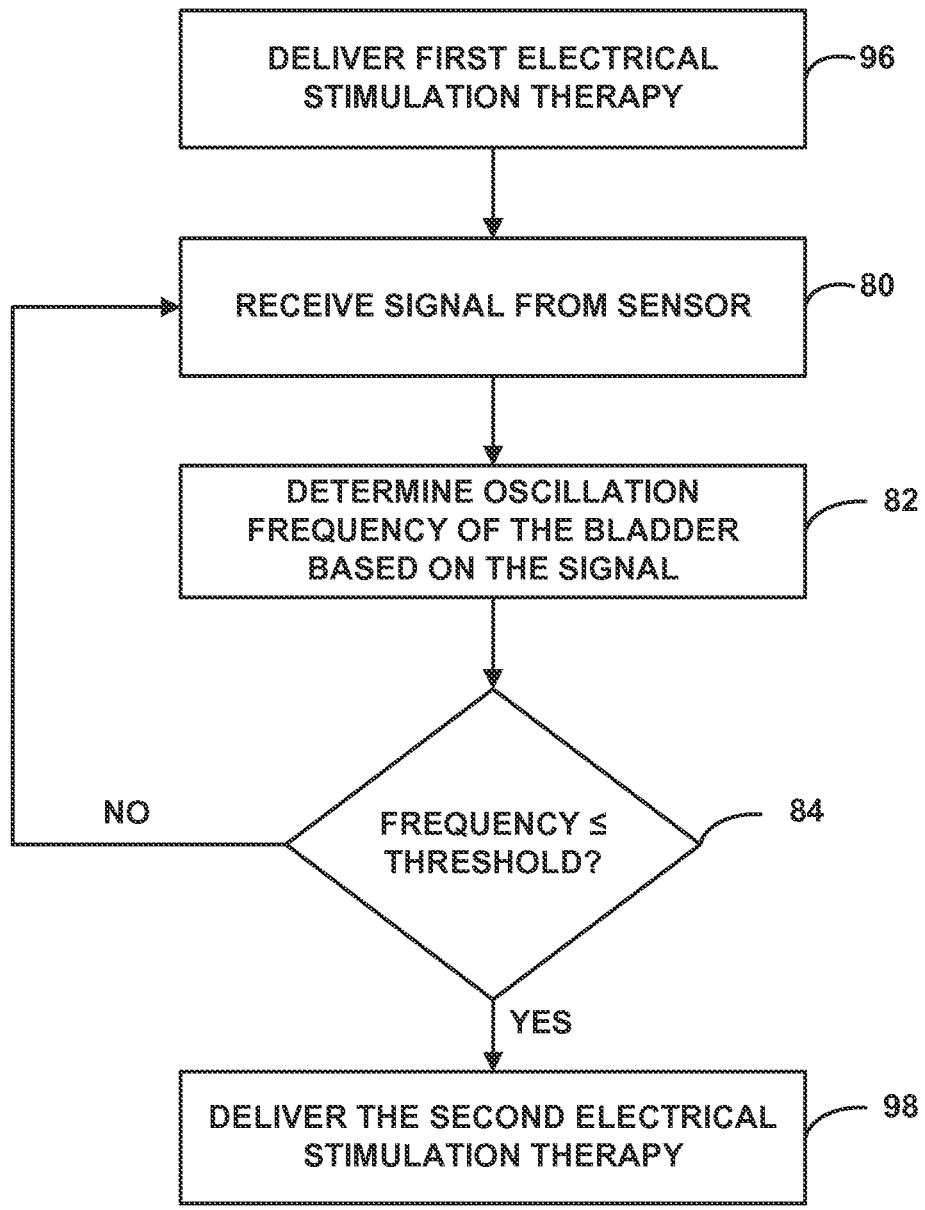
FIG. 10 is a flow diagram of an example technique for controlling the delivery of first and second stimulation therapies to a patient based on an oscillation frequency of a bladder of the patient.

In another example, as discussed with respect to FIG. 10, IMD 22 may be configured to deliver a first stimulation therapy to elicit a first physiological response from patient 16 that helps prevent the occurrence of an involuntary voiding event and, in response to detecting a oscillation frequency of bladder 14 that is less than or equal to a predetermined threshold value, initiate delivery of a second stimulation therapy to elicit a second physiological response from patient 16 that helps prevent the occurrence of an involuntary voiding event. The first and second physiological responses are different, and in some examples, involve the activation of different muscles.

For example. IMD 22 may deliver the first stimulation therapy to patient 16 on a regular basis, e.g., to reduce bladder contractions, and, when an oscillation frequency less than or equal to a threshold value is detected, suspend the delivery of the first stimulation therapy and deliver the second stimulation therapy, e.g., to promote closure of a urinary sphincter. In this way, IMD 22 may deliver the second stimulation therapy upon the detection of an elevated bladder fullness level (as indicated by the oscillation frequency) indicative of a high probability that an involuntary voiding event will occur. The second stimulation therapy may provide a safeguard in addition to the primary incontinence therapy (i.e., the first stimulation therapy) against the occurrence of an involuntary voiding event. Thus, the second stimulation therapy may provide an additional "boost" of therapy, which may provide an increased protection against the occurrence of involuntary voiding events when needed or desired.

Programmer 28 is a device configured to communicate with IMD 22, and can be, for example, a key fob or a wrist watch, handheld computing device, computer workstation, or networked computing device. Programmer 28 includes a user interface that is configured to receive input from a user (e.g., patient 16, a patient caretaker or a clinician). In some examples, the user interface includes, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 28 can additionally or alternatively include a peripheral pointing device, such as a mouse, via which a user may interact with the user interface. In some examples, a display of programmer 28 may include a touch screen display, and a user may interact with programmer 28 via the display. In some examples, the user may also interact with programmer 28 and/or IMD 22 remotely via a networked computing device.

A user, such as a physician, technician, surgeon, electrophysiologist, or other clinician, may interact with programmer 28 or another separate programmer (not shown), such as a programmer, to communicate with IMD 22. Such a user may interact with a programmer to retrieve physiological or diagnostic information from IMD 22. For example, the user may use programmer 28 to retrieve information from IMD 22 regarding the oscillation frequency of patient 16 determined at one or more points in time, the pattern in the sensed oscillation frequency over time, responsive actions taken by IMD 22, sensor 12, or another device in response to detecting a particular oscillation frequency, and the like. As another example, the user may use a programmer to retrieve information from IMD 22 regarding the performance or integrity of IMD 22 or other components of system 20, such as leads 24, 26, or a power source of IMD 22. In some examples, this information may be presented to the user as an alert if a system condition that may affect the efficacy of therapy is detected.

The user may also interact with programmer 28 to program IMD 22, e.g., select values for the stimulation parameters with which IMD 22 generates and delivers stimulation and/or the other operational parameters of IMD 22. For example, with the aid of programmer 28, different sets of therapy parameter values (referred to herein as therapy programs) for each of the first and electrical stimulation therapies may be selected for patient 16, e.g., by testing a plurality of therapy programs on patient 16 and determining which therapy programs elicits the desired physiological response from patient 16 for mitigating or even eliminating symptoms or conditions associated with the lower urinary tract dysfunction.

In some examples, patient 16 may interact with programmer 28 to control IMD 22 to manually deliver the electrical stimulation therapy, to manually abort the delivery of a currently delivered electrical stimulation therapy by IMD 22, or to inhibit the delivery of any electrical stimulation therapy by IMD 22, e.g., during voluntary voiding events. When IMD 22 receives the input from programmer 28, IMD 22 may suspend delivery of electrical stimulation therapy for a predetermined period of time, e.g., two minutes, to allow patient 16 to voluntarily void.

In addition to or instead of interacting with programmer 28 to control therapy delivery, in some examples, patient 16 may interact directly with IMD 22 to control IMD 22 deliver electrical stimulation therapy to any one or more of manually abort the delivery of a currently delivered electrical stimulation therapy by IMD 22 or temporarily inhibit the delivery of any electrical stimulation therapy by IMD 22, e.g., during voluntary voiding events. For example, a motion sensor can be integrated into or on a housing of IMD 22, and the motion sensor can generate a signal that is indicative of patient 16 tapping IMD 22 through the skin. The number, rate, or pattern of taps may be associated with the different user inputs, and a processor of IMD 22 may identify the tapping by patient 16 to determine when user input is received, what action should be taken in response to receiving the input (e.g., by determining instructions associated with the particular user input), and take a responsive action consistent with the user input.

In some examples, programmer 28 provides a notification to patient 16 that indicates whether electrical stimulation therapy is currently being delivered to patient 16 or notify patient 16 of the prospective delivery of electrical stimulation therapy to provide patient 16 with the opportunity to manually abort the prospective delivery of therapy. In such examples, programmer 28 may display a visible message, emit an audible alert signal or provide a somatosensory alert (e.g., by causing a housing of programmer 28 to vibrate). After generating the notification, programmer 28 may wait for input from patient 16 prior to delivering the stimulation therapy. Patient 16 may enter input that either confirms delivery of the indicated electrical stimulation therapy, or manually aborts the prospective delivery of the indicated electrical stimulation therapy. In the event that no input is received within a particular range of time, programmer 28 may, for example, wirelessly transmit a signal that indicates the absence of patient input to IMD 22. IMD 22 may then elect to deliver or not to deliver the stimulation therapy based on the programming of IMD 22.

Sensor 12, IMD 22, and programmer 28 may communicate with each other via wireless communication using any techniques known in the art. Examples of communication techniques may include, for example, low frequency or radiofrequency (RF) telemetry, but other techniques are also contemplated. In some examples, programmer 28 may include a programming head that may be placed proximate to the patient's body near sensor 12 implant site, IMD 22 implant sit, or both, in order to improve the quality or security of communication between programmer 28 and the implanted device 12 or 22.

System 20 shown in FIG. 2 is merely one example of a therapy system that is configured to sense mechanical oscillations of bladder 14 and control therapy delivery to patient 16 based on the frequency of the sensed mechanical oscillations. Systems with other configurations of leads, electrodes, and sensors are possible. For example, in other implementations, IMD 22 may be coupled to additional leads or lead segments having one or more electrodes positioned at different locations proximate the spinal cord or in the pelvic region of patient 16. The additional leads may be used for delivering different stimulation therapies to respective stimulation sites within patient 16 or for monitoring at least one physiological parameter of patient 16.

Additionally, in other examples, a system may include more than one IMD. For example, a system may include two IMDs coupled to respective one or more leads. Each IMD can deliver stimulation to a respective lateral side of patient 16 in some examples. In addition, sensor 12 can be external to patient 16 or incorporated into a common housing as IMD 22 in some examples, and multiple sensors can be used to sense mechanical oscillations of bladder 14 of patient 16.

As another example configuration, a therapy system can include one or more microstimulators in addition to IMD 22 and leads 24, 26. The microstimulators may have a smaller form factor than IMD 22 and may not be coupled to any separate leads. Rather, the microstimulators may be leadless and configured to generate and deliver electrical stimulation therapy to patient 16 via one or more electrodes on an outer housing of the microstimulators. The microstimulators can be implanted at various locations within the pelvic floor and at different target tissue sites within patient 16. IMD 22 or another microstimulator may act as a "master" module that coordinates the delivery of stimulation to patient 16 via the plurality of microstimulators.

Figure 3:
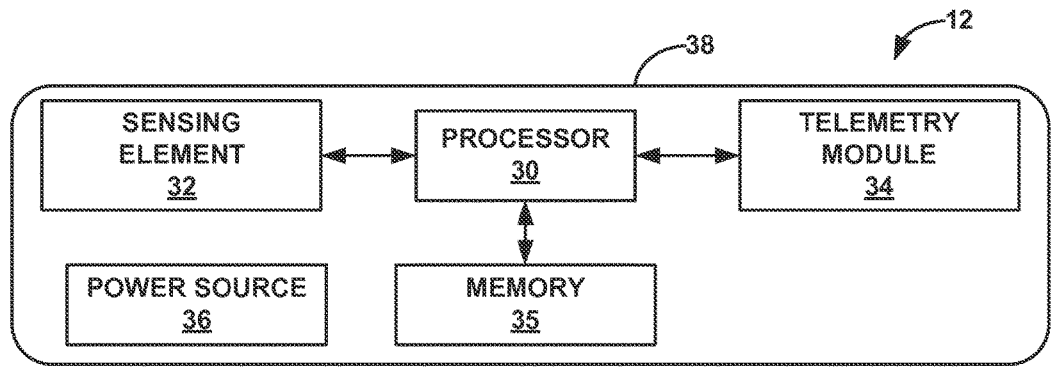
FIG. 3 is a block diagram illustrating an example configuration of the sensor of FIGS. 1 and 2.

FIG. 3 is a functional block diagram of an example sensor 12, which includes processor 30, sensing element 32, telemetry module 34, memory 35, and power source 36. In other examples, sensor 12 may include a fewer or greater number of components. Sensor 12 further includes outer housing 38 which is configured to substantially enclose (e.g., fully enclose or nearly fully enclose) the components of sensor 12, including processor 30, sensing element 32, telemetry module 34, memory 35, and power source 36. Outer housing 38 may be comprised of any suitable material, such as a biocompatible titanium or polymer. In some examples, outer housing 38 may be hermetically sealed in order to protect the components of sensor 12 from environmental contaminants.

Sensing element 32 may be any suitable mechanism that is configured to sense mechanical oscillations of bladder 14 (FIG. 1) of patient 16. In one example, sensing element 32 comprises an acoustic or pressure sensor that is configured to generate an electrical signal that changes as a function of pressure waves generated in patient 16 produced by mechanical oscillations of bladder 14 and incident on an outer housing of sensor 12. In these examples, sensing element 32 may include a pressure transducer (e.g., a capacitive, resistive or optical pressure transducer) or other element capable of producing and detecting vibrations of an outer housing of sensor 12 corresponding to pressure waves within patient 16. Example transducers may include electroactive polymers, microelectromechanical systems, accelerometers, or piezoelectric crystals.

In another example, sensing element 32 comprises a force sensor or a load cell that generates a signal indicative of a force or load, respectively, applied to outer housing 38 of sensor 12. The force or load applied to the outer housing of sensor 12 may fluctuate with the occurrence of mechanical bladder oscillations, such that the frequency of the change in force or load may be used as a surrogate for the bladder oscillation frequency.

In another example, sensing element 32 comprises a displacement sensor. Outer housing 38 of sensor 12 or a portion of outer housing 38 of sensor 12 may be displaced with the same frequency as mechanical bladder oscillations, such that the frequency of the displacement of the outer housing of sensor 12 or the portion of outer housing 38 may be used as a surrogate for the bladder oscillation frequency.

In another example, sensing element 32 comprises a flexible printed circuit comprising pressure sensitive ink and incorporated within outer housing 38 of sensor 12. The flexible printed circuit board is relative small and flexible, which may enable the circuit to adapt to different surface profiles. The pressure sensitive ink may exhibit different resistances depending on the load applied to outer housing 38 of sensor 12, which may change depending on the mechanical oscillations of bladder 14.

Other suitable sensing elements include, but are not limited to, other types of analog resistance or voltage based sensors. In addition, in some examples, sensing element 32 comprises any combination of the sensing elements described above.

Processor 30 is configured to receive a signal generated by sensing element 32. In some examples, processor 30 determines the frequency of mechanical oscillations of bladder 14 based on the signal. In these examples, processor 30 may transmit the determined oscillation frequency to another device, such as external device 18, programmer 28, or IMD 22 via telemetry module 34. In other examples, processor 30 is configured to transmit a signal indicative of the oscillation frequency of bladder 14 to the other device, where the signal may be a raw signal generated by sensing element 32 or a signal to which processor 30 has processed. In some examples, processor 30 processes the signal from sensing element 32 by applying a band pass filter, a low-pass filter, or a high-pass filter. The parameters of the filter of sensor 12 and of other components described herein may be selected based on the frequency range of the portion of the signal generated by sensing element 32 that changes as a function of the mechanical oscillations of bladder 14, such that the signal output from the filter is the portion of the signal generated by sensor 32 relevant to determining the bladder oscillation frequency.

Telemetry module 34 includes any suitable hardware, firmware, software or any combination thereof for communicating with another device, such as external device 18, programmer 28, or IMD 22. Under the control of processor 30, telemetry module 34 may receive downlink telemetry from and send uplink telemetry, e.g., an alert, to the other device with the aid of an antenna, which may be internal and/or external. Processor 30 may provide the data to be uplinked to the telemetry module 34, and receive data from telemetry module 34.

Sensor 12 comprises any suitable arrangement of hardware, alone or in combination with software and/or firmware, to perform the techniques attributed to processor 30, sensing element 32, telemetry module 24, and memory 35 herein. The processors described in this disclosure, including processor 30, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof.

Memory 35 may also store instructions for execution by processor 30. In addition, in some cases, under the control of processor 30, information related to sensed bladder oscillations, such as the frequency of bladder oscillations or the signal generated by sensing element 32, may be recorded by memory 35 for long-term storage and retrieval by a user. Memory 35, as well as other memories described herein, may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 35 may store program instructions that, when executed by processor 30, cause sensor 12 to perform the functions ascribed to sensor 12 herein. In addition, memory 35 may store information for determining a bladder fullness level based on sensed bladder oscillations, such as one or more oscillation frequency values associated with particular bladder fullness states (e.g., a low fullness state, an elevated fullness state, or both).

Power source 36 is configured to deliver operating power to the components of IMD 20. Power source 36 may include a battery and a power generation circuit to produce the operating power. In some examples, the battery may be rechargeable to allow extended operation. Recharging may be accomplished through proximal inductive interaction between an external charger and an inductive charging coil within sensor 12.

Figure 4:
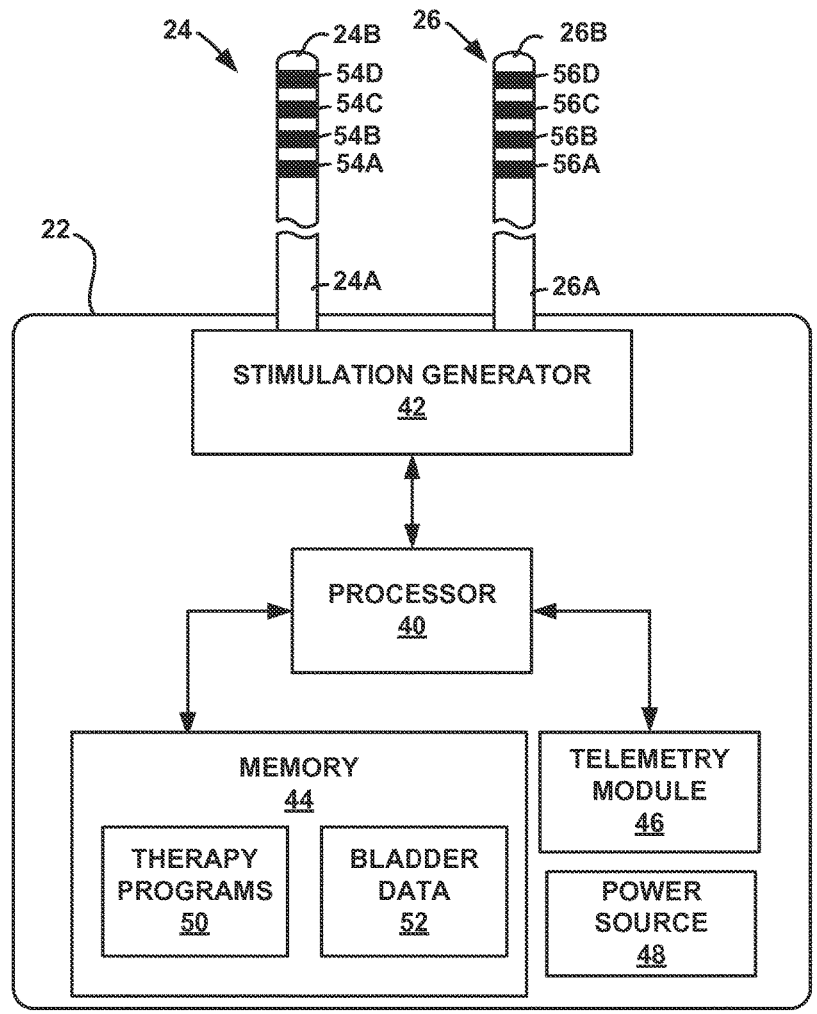
FIG. 4 is a block diagram illustrating an example configuration of an example IMD, which may be a part of the system of FIG. 2.

FIG. 4 is a block diagram illustrating example components of IMD 22. In the example of FIG. 4, IMD 22 includes processor 40, stimulation generator 42, memory 44, telemetry module 46, and power source 48. In other examples, IMD 22 may include a fewer or greater number of components. For example, in some examples, sensor 12 can be a part of IMD 22 and substantially enclosed within the same outer housing as stimulation generator 42 or IMD 22 may include a sensing module electrically connected to leads 24, 26 and configured to sense one or more physiological parameters of patient 16 via electrodes of leads 24, 26.

In the example shown in FIG. 4, leads 24, 26 are electrically coupled to stimulation generator 42, such that stimulation generator 42 may deliver electrical stimulation signals to patient 16 via any subset of electrodes 54A-54D (collectively referred to as "electrodes 54") of lead 16 and electrodes 56A-56D (collectively referred to as "electrodes 56") of lead 26. A proximal end 24A, 26A of each lead 24, 26, respectively, extends from the outer housing of IMD 22 and a distal end 24B, 26B of each lead 24, 26, respectively, extends to a target therapy site.

In the example shown in FIG. 4, leads 24, 26 are cylindrical. Electrodes 54, 56 of leads 24, 26, respectively, may be ring electrodes, segmented electrodes, partial ring electrodes or any suitable electrode configuration. Segmented and partial ring electrodes each extend along an arc less than 360 degrees (e.g., 90-120 degrees) around the outer perimeter of the respective lead 24, 26. In some examples, segmented or partial ring electrodes may be useful for targeting different fibers of the same or different nerves to elicit different physiological effects. In other examples, one or more of leads 24, 26 may be, at least in part, paddle-shaped (i.e., a "paddle" lead), and may include an array of electrodes on a common surface, which may or may not be substantially flat.

In some examples, one or more of electrodes 54, 56 may be cuff electrodes that are configured to extend at least partially around a nerve (e.g., extend axially around an outer surface of a nerve). Delivering stimulation via one or more cuff electrodes and/or segmented (or partial ring) electrodes may help achieve a more uniform electrical field or activation field distribution relative to the nerve, which may help minimize discomfort to patient 16 that results from the delivery of electrical stimulation therapy. An electrical field may define the volume of tissue that is affected when the electrodes 54, 56 are activated. An activation field represents the neurons that will be activated by the electrical field in the neural tissue proximate to the activated electrodes.

In general, IMD 22 comprises any suitable arrangement of hardware, alone or in combination with software and/or firmware, to perform the techniques attributed to IMD 22 and processor 40, stimulation generator 42, and telemetry module 46 of IMD 22. In various examples, processor 40 can include any one or more microprocessors, DSPs, ASICs, FPGAs, or any other equivalent integrated or discrete logic circuitry, as well as any combinations of such components. IMD 22 may also include a memory 44, which include any volatile or non-volatile media, such as RAM, ROM, NVRAM, EEPROM, flash memory, and the like. Although processor 40, stimulation generator 42, and telemetry module 46 are described as separate modules, in some examples, processor 40, stimulation generator 42, and telemetry module 46 can be functionally integrated. In some examples, processor 40, stimulation generator 42, telemetry module 46 correspond to individual hardware units, such as ASICs, DSPs, FPGAs, or other hardware units.

Memory 44 stores stimulation therapy programs 50 that specify stimulation parameter values for the stimulation therapy provided by IMD 22. Stimulation generator 42 is configured to generate and deliver electrical stimulation therapy according to stimulation parameter values defined by a therapy program. In this way, a therapy program may define the electrical stimulation therapy delivered to patient 16. In some examples, stimulation generator 42 delivers therapy in the form of electrical pulses. In such examples, relevant stimulation parameters for each therapy program 50 may include a voltage amplitude, a current amplitude, a pulse rate, a pulse width, a duty cycle, or the combination of electrodes 54, 56 with which stimulation generator 42 delivers the stimulation signals to tissue of patient 16. In other examples, stimulation generator 42 delivers electrical stimulation in the form of continuous waveforms. In such examples, relevant stimulation parameters may include a voltage amplitude, a current amplitude, a frequency, a shape of the stimulation signal, a duty cycle of the stimulation signal, or the combination of electrodes 54, 56 with which stimulation generator 42 delivers the stimulation signals to tissue of patient 16.

Under the control of processor 40, stimulation generator 42 is configured to deliver electrical stimulation to tissue of patient 16 via selected electrodes 54, 56 carried by leads 24, 26, respectively. In some examples, processor 40 controls stimulation generator 42 by selectively accessing and loading at least one of therapy programs 50 from memory 44 to stimulation generator 42. Stimulation generator 42 includes any suitable number of independently controllable stimulation channels, such as one, two, or more than two independently controllable stimulation channels.

In examples in which IMD 22 delivers a first stimulation therapy and, in response to detecting an oscillation frequency of bladder 14 (FIG. 1) that is less than or equal to a threshold value, delivers a second stimulation therapy, stimulation therapy programs 50 include one or more stimulation therapy programs for each of the first and second stimulation therapies. The therapy programs associated with the first and second stimulation therapies may differ from each other by at least one stimulation parameter value. In other examples, IMD 22 is configured to deliver only the first stimulation therapy and may, for example, initiate delivery of the first stimulation therapy to patient 16 in response to detecting an oscillation frequency of bladder 14 that is less than or equal to a threshold value or adjust a stimulation parameter value that defines the first stimulation therapy in response to detecting an oscillation frequency of bladder 14 that is less than or equal to a threshold value.

In some examples, the stimulation parameter values for therapy programs 50 that define the first electrical stimulation therapy may be selected to relax the patient's bladder, e.g., to reduce a bladder contraction frequency. Example range of stimulation parameters for the first stimulation therapy that are may be effective in treating incontinence, e.g., when applied to the sacral or pudendal nerves, are as follows:

1. Frequency: between approximately 0.5 Hertz (Hz) and approximately 500 Hz, such as between approximately 10 Hz and approximately 250 Hz, or between approximately 8 Hz and approximately 25 Hz.

2. Amplitude: between approximately 0.1 volts and approximately 50 volts, such as between approximately 0.5 volts and approximately 20 volts, or between approximately 1 volt and approximately 10 volts.

3. Pulse Width: between approximately 10 microseconds (μs) and approximately 5000 μs, such as between approximately 100 μs and approximately 1000 μs, or between approximately 180 μs and approximately 450 μs.

Stimulation parameter values the therapy programs 50 that define the second stimulation therapy (if applicable) may be selected to maximize closure of one or more of internal urinary sphincter, external urinary sphincter, and periurethral muscles. Stimulation parameter values for the second stimulation therapy may also be selected to minimize muscle fatigue. Muscle fatigue may occur when the force-generating ability of a muscle decreases as a result of the electrical stimulation. An example range of stimulation parameter values for the one or more therapy programs 50 that define the second stimulation therapy are as follows:

1. Frequency: between approximately 15 Hz to approximately 30 Hz to activate slow-twitch muscles to minimize muscle fatigue while providing some sphincter closure, and between approximately 30 Hz and approximately 66 Hz to activate fast-twitch muscles, which may maximize sphincter closure.

2. Amplitude: approximately 2-8 times rheobase (e.g., approximately 2-4 times rheobase) for the target nerve or muscle (e.g., the sphincter muscle), such as about 0.5 volts to about 50 volts, or about 0.5 volts to about 10 volts, or about 4 volts to about 8 volts. Rheobase is the minimal electric current of infinite duration that results in an action potential or muscle twitch.

3. Pulse Width: between about 10 microseconds (μs) and about 5,000 μs, such as between about 100 μs and approximately 1,000 μs.

Additionally, in some examples, the stimulation parameter values for one or more of the first and second stimulation therapies may include the parameter values that define a therapy cycle, which includes a first time period ("on" periods) during which IMD 22 actively delivers a stimulation signal to patient 16 and a second time period ("off" periods), during which IMD 22 does not deliver any stimulation to patient 16. When stimulation generator 42 delivers the stimulation therapy according to such a therapy cycle, a stimulation signal is not continuously delivered to patient 16, but periodically delivered (e.g., only during the first time period). The first and second time periods may have durations on the order of minutes, but can be longer or shorter depending on the particular patient 16.

In some examples, memory 44 stores bladder data 52, which may include information related to sensed mechanical oscillations of bladder (e.g., detected oscillation frequencies), which may be recorded for long-term storage and retrieval by a user, or used by processor 40 for adjustment of stimulation parameters, such as amplitude, pulse width, and pulse rate. Bladder data 52 may also include information used by processor 40 to take a responsive action based on a sensed oscillation frequency of bladder 14. For example, bladder data 52 may include one or more predetermined threshold values for an oscillation frequency of bladder 14 that are used to control the timing of a responsive action taken by processor 40 or another device (e.g., a processor of external device 18, programmer 28, or sensor 12).

As an example, bladder data 52 can include one or more predetermined oscillation frequency threshold values (also referred to herein as "thresholds" or "threshold values") for initiating the delivery of the stimulation therapy (the first or second, depending on the example) or for adjusting the delivery of electrical stimulation that is currently being actively delivered to patient 16. The one or more oscillation frequency threshold values used to control delivery of the first electrical stimulation therapy may, for example, be associated with a bladder fullness level that indicates a patient condition for which electrical stimulation therapy or an adjustment to electrical stimulation therapy may be desirable to help prevent the occurrence of an involuntary voiding event. The one or more oscillation frequency threshold values used to control the second electrical stimulation therapy (in examples in which IMD 22 is configured to deliver the first and second stimulation therapies) may, for example, be associated with a bladder fullness level that indicates a patient condition for which an additional boost of electrical stimulation therapy may be desirable to help prevent the occurrence of an involuntary voiding event.

In some examples, bladder data 52 also stores one or more threshold oscillation frequency values with which processor 40 may control the duration of a therapy period during which the first or second electrical stimulation therapy is delivered to patient 16. For ease of description, this threshold value may be referred to as a "second threshold value." The second threshold value may be selected to indicate a bladder fullness level at which there is a lower likelihood of an involuntary voiding event, such that the electrical stimulation therapy delivered in response to detecting a previous relatively high bladder fullness level may be suspended or otherwise adjusted. In this way, processor 40 may use threshold values stored as bladder data 52 to control stimulation generator 42.

The threshold values stored by memory 44 and are used by processor 40 to control the delivery of the electrical stimulation therapy may be determined by a clinician, e.g., during a learning phase in which the oscillation frequencies of bladder 14 are correlated with a micturition cycle of patient 16. A single micturition cycle occurs between two voiding events, such that the bladder fullness level may gradually increase during the micturition cycle. Various parameters relating to the micturition cycle of patient 16 may be determined during the learning phase. Examples parameters include, for example, the mean, median, shortest or longest duration between voiding events. Based on this data, and, in some examples, other physiological data sensed during the learning phase (e.g., bladder impedance values or EMG activity of bladder 14, which may indicate the bladder fullness level), one or more bladder fullness levels of patient 16 may be associated with respective oscillation frequencies of bladder 14.

In some cases, regardless of whether the fullness level of bladder 14 may be considered to linearly or nonlinearly increase during a micturition cycle, a plurality of oscillation frequencies of bladder 14 may be determined during a micturition cycle and the threshold value stored by memory 44 may be selected to be the oscillation frequency observed at a particular point in the micturition cycle at which the responsive action is desired. For example, in some examples, the clinician may select or a processor of a device, such as programmer 28, may automatically select the oscillation frequency at a point about 50% to about 75% through the micturition cycle as the threshold value for initiating the delivery of the first stimulation therapy. The threshold oscillation frequency value may be based on a plurality of micturition cycles and may be, for example, the mean, median, lowest, or highest oscillation frequency observed at the particular point in the micturition cycle.

In examples in which IMD 22 delivers first and second stimulation therapies to patient 16, the threshold oscillation frequency value based on which processor 40 controls stimulation generator 42 to generate and deliver the second stimulation therapy to patient 16 may be determined in a similar manner as the technique described above. For example, a clinician may select or a processor of a device may automatically select the oscillation frequency observed at a point in time in a micturition cycle (e.g., about 75% to 90% of the way through the micturition cycle) when an additional boost of therapy delivery may be desirable to help prevent the occurrence of an involuntary voiding event as the threshold oscillation frequency value used to control the delivery of the second stimulation therapy. The threshold oscillation frequency value used to control the delivery of the second stimulation therapy may be determined based on a plurality of observed micturition cycles and can be, for example, the mean, median, lowest, or highest oscillation frequency at the particular point in time for a plurality of micturition cycles.

Other techniques for determining the threshold oscillation frequency values for controlling the first stimulation therapy, the second stimulation therapy, or both, may also be used. One threshold oscillation frequency may be selected to be the frequency at which there may be an elevated bladder fill level, such that electrical stimulation therapy, an adjustment to therapy or an additional boost of electrical stimulation therapy (if electrical stimulation therapy is already being delivered to patient 16) is desirable to help prevent the occurrence of an involuntary voiding event. In some examples, processor 40 may periodically update the threshold values stored as bladder data 52, e.g., based on clinician input or based on information indicating the micturition cycles of patient 16 have changed or the current threshold values are not resulting in effective therapy delivery to patient 16.

In examples in which stimulation generator 42 adjusts the electrical stimulation therapy based on a sensed oscillation frequency of bladder 14, bladder data 52 can include instructions for execution by processor 40 to adjust electrical stimulation parameters based on a sensed oscillation frequency of bladder 14. Memory 44 may also store instructions for execution by processor 40, in addition to stimulation therapy programs 50 and bladder data 52. In some examples, memory 44 includes separate memories for storing instructions, electrical signal information, therapy programs 50, and bladder data 52.

In examples in which processor 40 controls stimulation generator 42 to initiate the delivery of electrical stimulation therapy or adjust the electrical stimulation therapy in response to detecting an oscillation frequency of bladder 14 than is less than or equal to a threshold value stored by memory 44, processor 40 may continue to deliver the stimulation therapy (or the adjusted stimulation therapy) until a particular event is detected. That is, processor 44 may control the therapy period during which the stimulation therapy is delivered to patient 16 based on one or more events. The event may be, for example, a detected oscillation frequency of bladder 14 that is greater than the stored threshold value that was used to initiate the electrical stimulation therapy delivery or the adjustment to the stimulation therapy. In another example, the event may be a detected oscillation frequency of bladder 14 that is greater than a second threshold value that is associated with a bladder fullness level at which there is a lower likelihood of an involuntary voiding event. In some examples, the second threshold value is greater than the first threshold value that was used to initiate the first stimulation therapy delivery or the adjustment to the first stimulation therapy.

As another example, the event may be a particular duration of time, which may be selected by a clinician and stored by memory 44. Another example of an event may be user input (e.g., received via programmer 28 and transmitted to IMD 22 or directly received by IMD 22) that indicates a recent voiding event, such that the fill level of bladder 14 is lower and termination of the electrical stimulation therapy or adjustment back to a different therapy program is appropriate. The event may also be any one or more of the aforementioned events.

Similarly, in examples in which processor 40 controls stimulation generator 42 to generate and deliver a first electrical stimulation therapy and initiate delivery of a second stimulation therapy in response to detecting an oscillation frequency of bladder 14 than is less than or equal to a threshold oscillation frequency value stored by memory 44, processor 44 may continue to deliver the second stimulation therapy until a particular event is detected. The event may be any one or more of aforementioned events. In response to detecting the event, processor 40 may control stimulation generator 40 to suspend or adjust the second electrical stimulation therapy.

Telemetry module 46 includes any suitable hardware, firmware, software or any combination thereof for communicating with another device, such as programmer 28 (FIG. 1). Generally, processor 40 controls telemetry module 46 to exchange information with medical device programmer 28 and/or another device external to IMD 22. Under the control of processor 40, telemetry module 46 may receive downlink telemetry, e.g., patient input, from and send uplink telemetry, e.g., an alert, to programmer 28 with the aid of an antenna, which may be internal and/or external. Processor 40 may provide the data to be uplinked to programmer 28 and the control signals for the telemetry circuitry within telemetry module 46, and receive data from telemetry module 46. Processor 40 may transmit operational information and receive stimulation programs or stimulation parameter adjustments via telemetry module 46. Also, in some examples, IMD 22 may communicate with other implanted devices, such as stimulators, control devices, or sensors, via telemetry module 46.

Processor 40 monitors input received via telemetry module 46 and takes appropriate action. As previously described, in some examples, telemetry module 46 may receive an indication from programmer 28 that patient 16 has voluntarily voided, and processor 40 may control stimulation generator 42 to adjust stimulation in response to receiving the input (e.g., may control stimulation generator 42 to terminate the delivery of the first electrical stimulation therapy or the second electrical stimulation therapy, or adjust the stimulation therapy and deliver stimulation to patient 16 in accordance with the adjusted stimulation parameter values).

Telemetry module 46 can also receive patient input indicating a voluntary voiding event. In response to receiving the input, if the first or second stimulation therapies are being delivered to patient 16, processor 40 may suspend delivery of the first stimulation therapy or the second stimulation therapy for a pre-determined period of time, e.g., 2 minutes.

Power source 60 delivers operating power to the components of IMD 22. Power source 60 may include a battery and a power generation circuit to produce the operating power. In some examples, the battery may be rechargeable to allow extended operation.

Figure 5:
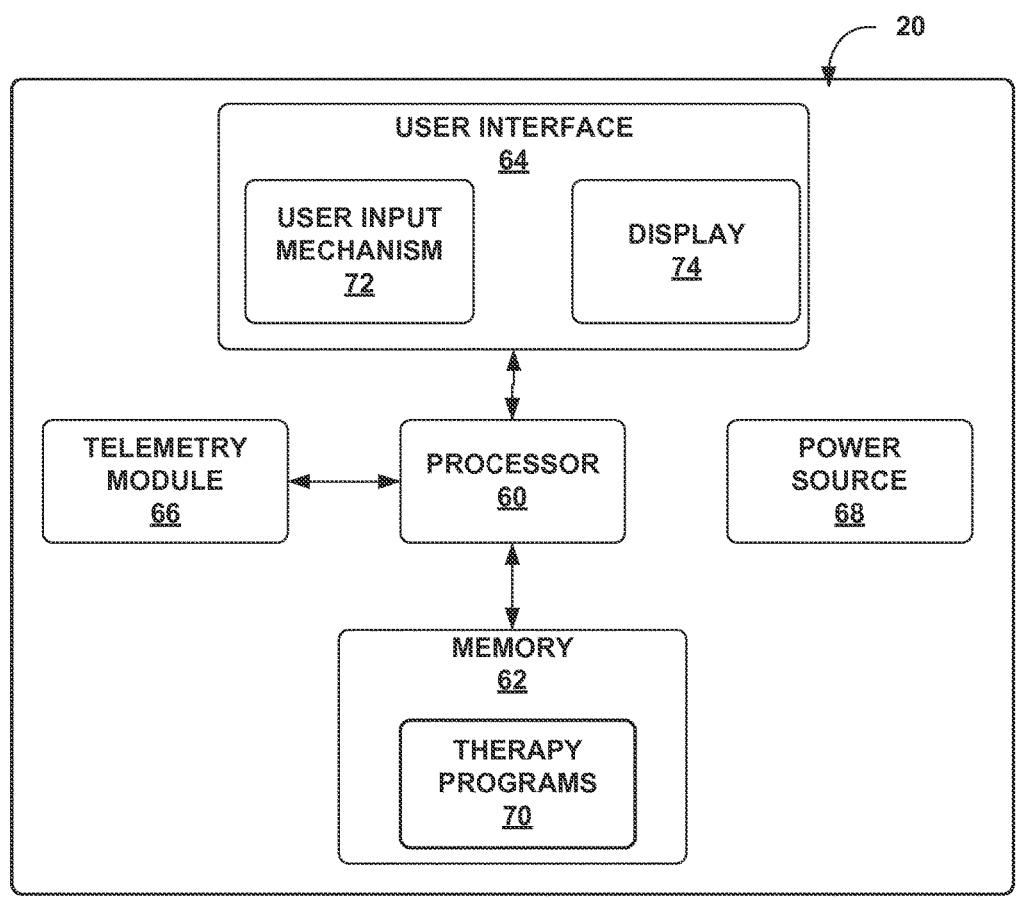
FIG. 5 is a block diagram illustrating an example configuration of an external device, such as an external programmer.

FIG. 5 is a functional block diagram illustrating example components of external medical device programmer 28. Programmer 28 may be a hand-held computing device, a notebook computer, a tablet computer, a consumer electronic device, such as a smart phone, a desktop computer, or a workstation, as examples. Programmer 28 may be a dedicated hardware device with dedicated software for programming of IMD 22. Alternatively, programmer 28 may be an off-the-shelf computing device running an application that enables programmer 28 to program IMD 22.

As illustrated in FIG. 5, programmer 28 may include a processor 60, memory 62, user interface 64, telemetry module 66, and power source 68. Programmer 28 comprises any suitable arrangement of hardware, alone or in combination with software and/or firmware, to perform the techniques attributed to programmer 28, and processor 60, user interface 64, and telemetry module 66 of programmer 28. In various examples, programmer 28 may include one or more processors, such as one or more microprocessors, DSPs, ASICs, FPGAs, or any other equivalent integrated or discrete logic circuitry, as well as any combinations of such components. Processor 60 is configured to control user interface 64 and telemetry module 66, and store and retrieve information and instructions to and from memory 62. Moreover, although processor 60 and telemetry module 66 are described as separate modules, in some examples, processor 60 and telemetry module 66 are functionally integrated.

Programmer 28 also, in various examples, may include a memory 62, such as RAM, ROM, PROM, EPROM, EEPROM, flash memory, a hard disk, a CD-ROM, a floppy disk, a cassette, magnetic media, or optical media. Memory 62 may store program instructions that, when executed by processor 60, cause processor 60 and external programmer 28 to provide the functionality ascribed to external programmer throughout this disclosure. In some examples, memory 62 may further include therapy information, e.g., therapy programs 70 defining electrical stimulation therapy delivered by IMD 22, e.g., similar or identical to therapy programs 50 (FIG. 4) described above with respect to memory 44 of IMD 22. In addition, memory 62 may, in some examples, store instructions for execution by processor 40 of IMD 22 for adjusting electrical stimulation parameters based on a sensed oscillation frequency of bladder 14. In some examples, memory 62 may also store bladder data similar or identical to bladder data 52 (FIG. 4) described above with respect to IMD 22.

In some examples, the actual settings for the therapy programs, e.g., the stimulation amplitude, pulse rate and pulse width data, are stored within therapy programs 70. In other examples, an indication of each therapy program, e.g., a single value associated with each therapy program, may be stored within therapy programs 70, and the actual parameters may be stored within memory 44 of IMD 22 (FIG. 4). The "indication" for each therapy program or group may include, for example, alphanumeric indications (e.g., Therapy Program Group A, Therapy Program Group B, and so forth). The stimulation programs and/or bladder data stored in memory 62 may be downloaded into memory 44 of IMD 22 or vice versa.

User interface 64 is configured to receive input from a user, such as patient 16 or a patient caretaker, and present information to the user. Processor 60 may present and receive information relating to stimulation therapy via user interface 64. In addition, as described with respect to FIG. 7, in some examples, processor 60 may generate and present a notification to patient 16 or a patient caretaker via user interface 64 based on a sensed bladder oscillation frequency value.

In the example shown in FIG. 5, user interface 64 includes user input mechanism 72 and display 74. User input mechanism 70 may include any suitable mechanism for receiving input from patient 16 or another user. Example mechanisms for receiving input may include, for example, an alphanumeric keypad, directional buttons that permit patient 16 to scroll up or down through a data display presented on display 74, select items shown on display 74, push buttons, soft-keys, a receiver configured to receive voice activated commands, other inputs activated by physical interactions, magnetically triggered inputs, contacts defined by a touch screen, or any other suitable user interface. In some examples, buttons of user input mechanism 54 may be reprogrammable. That is, during the course of use of patient programmer 28, the buttons of user input mechanism 72 may be reprogrammed to provide different programming functionalities as the needs of patient 16 changes or if the type of IMD 22 implanted within patient 16 changes.

Display 74 may include a monochrome or color display screen, such as a LCD or LED display or any other suitable type of display. Programmer 28 may present information related to stimulation therapy provided by IMD 22, as well as other information, such as historical data regarding the patient's condition and sensed bladder oscillation frequencies, and past usage of different stimulation therapy programs. Processor 60 monitors activity from input mechanism 72, and controls display 74 and/or IMD 22 function accordingly. In some examples, display 74 may be a touch screen that enables the user to select options directly from the display. In such cases, user input mechanism 72 may be part of display 74, although programmer 28 may include both a touch screen and user input mechanism 72. In some examples, user interface 64 may also include audio circuitry for providing audible instructions or sounds to patient 16 and/or receiving voice commands from patient 16.

Patient 16 may use patient programmer 28 to select therapy programs, generate new therapy programs or program groups, modify one or more therapy parameter values of a stored therapy program through individual or global adjustments, transmit a new therapy program to a medical device, such as IMD 22. In this way, patient 16 may interact with programmer 28 to control therapy delivery by IMD 22.

Telemetry module 66 supports wireless communication between IMD 22 and programmer 28 under the control of processor 60, and, in some cases, between sensor 12 and programmer 28 under the control of processor 60. Telemetry module 66 may also be configured to communicate with another computing device via wireless communication techniques, or direct communication through a wired connection. Telemetry module 66 may be substantially similar to telemetry module 46 described above. In some examples, telemetry module 66 may include an antenna, which may take on a variety of forms, such as an internal or external antenna. Examples of local wireless communication techniques that may be employed to facilitate communication between programmer 28 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 28 without needing to establish a secure wireless connection.

Power source 68 delivers operating power to the components of programmer 28. Power source 68 may include a battery and a power generation circuit to produce the operating power. In some examples, the battery may be rechargeable to allow extended operation.

IMD 22, programmer 28, or both, may control of the delivery of the electrical stimulation to patient 16. If external programmer 28 controls the stimulation, programmer 28 may transmit therapy programs for implementation by processor 40 to IMD 22. In addition, or instead, programmer 28 may transmit a signal to IMD 22 indicating that processor 40 should execute locally stored programs or therapy routines. In such a manner, control over the electrical stimulation may be distributed between IMD 22 and external programmer 28, or may reside in either one alone.

In some examples, external device 18 of system 10 (FIG. 1) may have a configuration similar to that of external programmer 28 shown in FIG. 5. However, external device 18 may not store therapy programs 70 in some examples, and may not be configured to communicate with an IMD in some examples.

Any one or more of processor 30 of sensor 12, processor 40 of IMD 22, processor 60 of programmer 28, or a processor of external device 18 may determine an oscillation frequency of bladder 14 based on a signal generated by sensor 12 and take a responsive action based on the determined oscillation frequency (also referred to herein as the "sensed oscillation frequency"). While examples are described herein in which the responsive action is taken in response to detecting an oscillation frequency that is less than or equal to a predetermined threshold value, in other examples, the responsive action may be taken based on an oscillation frequency of bladder 14 using other techniques.

For example, in some examples, therapy delivery to patient 16 (e.g., electrical stimulation therapy) or other responsive actions may be controlled (e.g., adjusted) on a continuous or nearly continuous basis based on the changing (e.g., increasing, decreasing, or both) bladder fullness indicated by the detected oscillation frequency of bladder 14. In these examples, delivery of a notification, initiation of therapy delivery, adjustment to one or more therapy delivery parameters, delivery of a second stimulation therapy, or other responsive actions may be taken based on the currently sensed oscillation frequency, or predicted bladder volume, rather than based on detection of a discrete event, e.g., a bladder oscillation frequency less than or equal to a threshold value as described with respect to FIG. 6 below. In some examples, processor 40 of IMD 22 or a processor of another device may periodically determine the oscillation frequency, e.g., based on the most recent data sensed by sensor 12, and then determine what responsive action should be taken based on the determined oscillation frequency. Memory 44 of IMD 22 or a memory of another device may store a data structure that associates a plurality of different oscillation frequency values (e.g., discrete values or a plurality of ranges of values) with respective responsive actions, and processor 40 may reference this information to determine what responsive action to take based on detected oscillation frequency of bladder 14. At least two of the responsive actions associated with respective bladder oscillation frequency values or ranges of values are different. The responsive action may be the responsive action associated with the detected oscillation frequency of bladder 14 in memory 44 (or a memory of another device).

Figure 6:
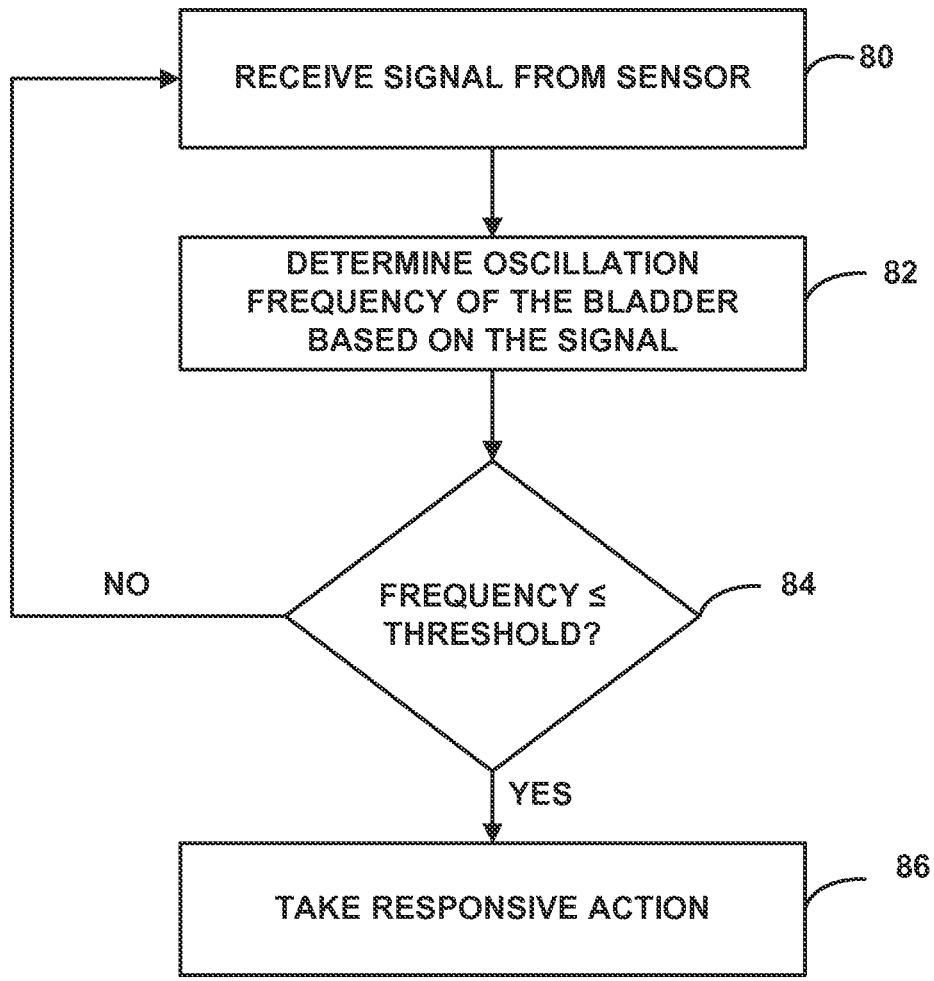
FIG. 6 is a flow diagram of an example technique for taking a responsive action based on an oscillation frequency of a bladder of a patient.

FIG. 6 is a flow diagram illustrating an example technique implemented by a system, such as system 10 (FIG. 1) or therapy system 20 (FIG. 2), for taking a responsive action based on an oscillation frequency of bladder 14 determined based on a signal generated by sensor 12. While FIGS. 6-10 are primarily described with respect to therapy system 20, in other examples, the techniques for taking a responsive action based on an oscillation frequency of bladder 14 may be implemented by other systems, which may include different components or configurations than therapy system 20. For example, system 10 (FIG. 1), which does not include a therapy delivery device, may implement the techniques in which the responsive action includes the generation of a notification to patient 16 or a patient caretaker. In addition, while particular processors are referred to in description of FIGS. 6-10, in other examples, a different combination of processors may perform the techniques shown in FIGS. 6-10.

In the technique shown in FIG. 6, processor 40 receives a signal from sensor 12 (80), where the signal changes as a function of the mechanical oscillations of bladder 14. The signal may be, for example, an electrical signal generated by processor 30 or sensing element 32 (FIG. 3) of sensor 12 and transmitted to IMD 22 via the respective telemetry modules 34, 46. In some examples, processor 40 receives the signal from sensor 12 on a substantially continuous basis (e.g., continuous or nearly continuous), or on a less frequent basis (e.g., once per minute). For example, processor 40 may periodically interrogate sensor 12 by transmitting to sensor 12, via the respective telemetry modules 46, 34, a request signal that requests processor 30 of sensor 12 transmit the signal indicative of the mechanical oscillations of bladder 12 to IMD 22. In response, processor 30 of sensor 12 may transmit the signal to processor 40 of IMD 22.

The signal transmitted by sensor 12 may have any suitable duration for determining a meaningful bladder contraction frequency of patient 16, such as about one second to about 30 seconds of sensor element recordings, or about five seconds to about 10 seconds of recordings. As indicated above, the oscillations in bladder 14 are caused by non-micturition contractions of bladder 14. Bladder 14 may not be oscillating at all times; thus, the signal from sensor 12 is long enough to capture the oscillations of bladder 14. Sensor 12, processor 40, or another component may include a hold function (e.g., on a transducer-filter of sensing element 32) in order to store data that will be recorded when bladder 14 is oscillating, thereby indicating the oscillation frequency of bladder 14.

After receiving the signal from sensor 12 (80), processor 40 may determine the oscillation frequency of bladder 14 based on the signal (82). For example, processor 40 may determine the fundamental frequency of the amplitude waveform of the signal from sensor 12. Processor 40 may determine the oscillation frequency of bladder 14 based on any suitable sample period of the signal. The duration of the sample period may be selected to provide a meaningful indication of the oscillation frequency of bladder 14. For example, the sample period may have a duration of about one second to about 4 minutes, or about 5 seconds to about 20 seconds, or about 10 seconds. Other durations are contemplated, such as durations less than one second or greater than 4 minutes. In some examples, processor 40 may determine the oscillation frequency of bladder 14 based on a portion of the received sensor signal that is indicative of the most recent bladder oscillations, e.g., sensed by sensor 12 within 30 seconds to about one minute of being received by processor 40.

Processor 40 may determine the oscillation frequency of bladder 14 at any suitable rate, such as once every second, once every five seconds, once every 30 seconds, once a minute, or even less frequently or more frequently. For example, processor 40 may continuously receive a signal from sensor 12 (80) and determine the oscillation frequency based on a sample of the signal from sensor 12 defined by a fixed window size (thereby defining the sample period of the signal). Processor 40 may move the sample window at regular time intervals along a digitized plot of the amplitude waveform of the signal from sensor 12. By moving the window at regular time intervals, multiple sample periods are defined. The rate at which processor 40 determines the oscillation frequency of bladder 14 may be a function of this time interval at which processor 40 moves the sample window.

Non-micturition contractions are one method of inducing mechanical oscillations in the bladder. Thus, bladder 14 may not oscillate at all times, but in response to the occurrence of non-micturition contractions. In some examples, in order to sense the bladder oscillations, non-micturition contractions may be detected by sensor 12 or a different sensor and, subsequently (e.g., shortly after non-micturition contractions end), sensor 12 may be used to measure the frequency of the mechanical oscillations in the bladder. A processor, such as processor 30 of sensor 12 or processor 40 of IMD 22 may then apply a filter (e.g., low pass or band-pass) to determine the frequency of bladder 14. As indicated above, this bladder oscillation frequency may be indicative of bladder volume. In some examples, the measured bladder volume with the time since the last voiding event (also referred to as a micturition event) may be used (e.g., by processor 40 or another processor) to measure urine rate. Bladder volume and urine rate may then be used to produce a bladder volume function that would predict bladder volume between measurements.

In some examples, processor 40 may determine the oscillation frequency of bladder 14 as close to real-time as permitted by the occurrence of non-micturition contractions and the configuration of system 20, e.g., taking into consideration the time required to transmit the signal from sensor 12 to processor 40. In this way, processor 40 may be determining a parameter indicative of real-time fullness of bladder 14. In order to achieve this, processor 40 may determine the oscillation frequency based on the most recent data sensed by sensor 12. The real-time or nearly real-time determination of the oscillation frequency may enable processor 40 to take an appropriate responsive action in a meaningful and timely manner, e.g., in response to the current fullness level of bladder 14. Even though the bladder oscillation frequency may decrease between the time processor 44 determines the oscillation frequency (82) based on the received sensor signal and takes a responsive action (86), which is discussed in further detail below, the fill level of bladder 14 may not change significantly enough during that time to cause the responsive action to be inappropriate for the current fullness level of bladder 14.

In some examples, processor 40 processes the signal from sensor 12 prior to determining the oscillation frequency (82). For example, if processor 40 receives an analog signal from sensor 12, processor 40 may digitize the signal. In other examples, processor 40 may receive a digitized signal from sensor 12. However, processor 40 may also determine bladder oscillation frequency based on an analog signal from sensor 12, without digitization. As another example of processing that may be used, processor 40 may apply a band pass filter, a high-pass filter, low-pass filter or the like to remove portions of the sensor signal attributable to sources other than the bladder oscillation. In other examples, processor 30 of sensor 12 processes the signal that changes as a function of bladder oscillations of patient 16 prior to transmitting the signal to processor 40 of IMD 22.

In some examples, processor 40 stores the determined oscillation frequency in memory 44 of IMD 22 or memory of another device (e.g., programmer 28 or a remote database). The determined oscillation frequency can be stored with other identifying information, such as the time at which the oscillation frequency was determined and, in some cases, the therapy parameters implemented by IMD 22 at the time the oscillation frequency was determined.

Processor 40 determines whether a responsive action should be taken based on the determined oscillation frequency of bladder 14. In the example shown in FIG. 6, processor 40 determines whether the determined oscillation frequency of bladder 14 is less than or equal a predetermined threshold value (84), which, as discussed above, may be stored by IMD 22, sensor 12, programmer 28 or another device. The oscillation frequency of bladder 14 decreases as the fullness level increases, such a sensed oscillation frequency of bladder 14 that is less than or equal to the predetermined threshold value may be indicative of a particular bladder fullness level, such as a relatively high bladder fullness level that may require patient 16 to void immediately or within a relatively short time frame (e.g., on the order of minutes, rather than hours). If the determined oscillation frequency of bladder 14 is not less than or equal to the threshold value ("NO" branch of block 84), processor 40 may continue receiving the signal from sensor 12 (80) and determining the oscillation frequency of bladder 14 based on the signal (82). On the other hand, if processor 40 determines that the determined oscillation frequency of bladder 14 is less than or equal to the threshold value ("YES" branch of block 84), processor 40 may take a responsive action (86).

Processor 40 make take one or more responsive actions in response to detecting an oscillation frequency of bladder 14 that is less than or equal to a predetermined threshold value. Examples of different responsive actions are described with respect to FIGS. 7-10, which each illustrate a flow diagram of an example of the technique shown in FIG. 6.

Figure 7:
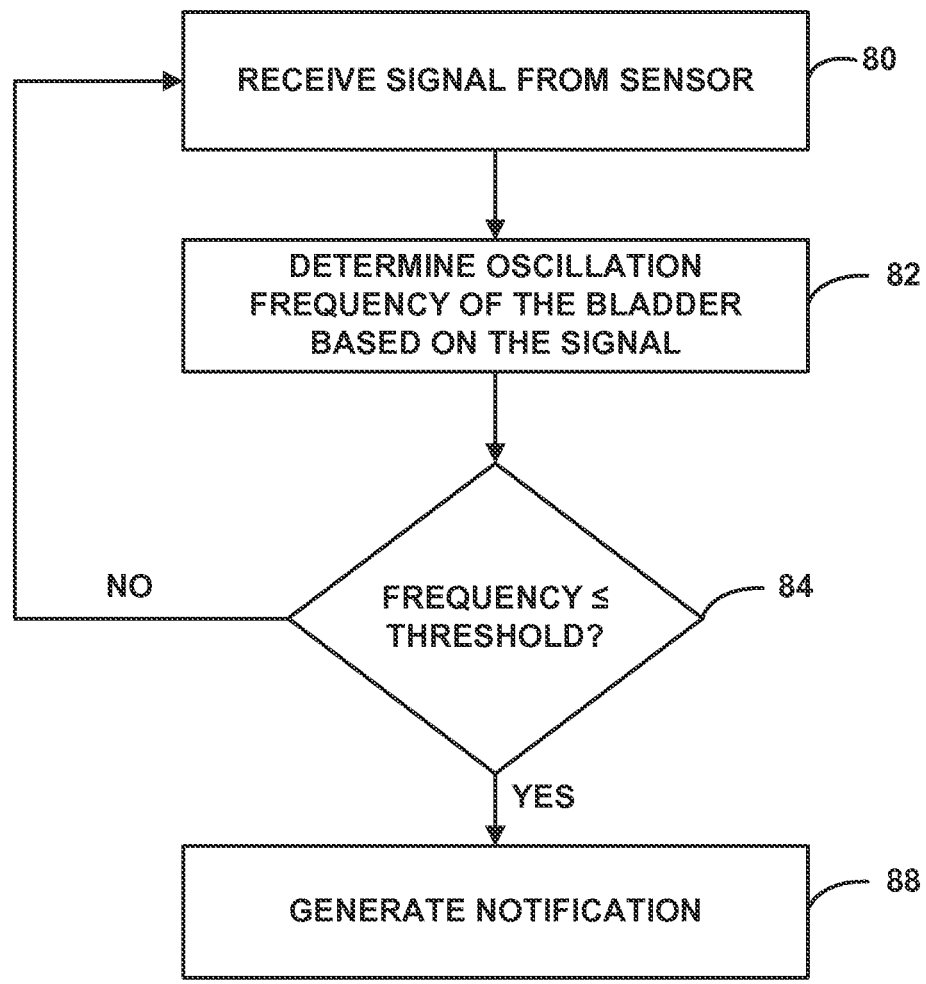
FIG. 7 is a flow diagram of an example technique for generating a notification based on an oscillation frequency of a bladder of a patient.

In the example technique shown in FIG. 7, after determining the oscillation frequency of bladder 14 is less than or equal to a predetermined threshold value ("YES" branch of block 84), processor 40 generates a notification (e.g., to patient 16 or a patient caretaker) (88). In one example, processor 40 generates the notification by causing a portion IMD 22 to vibrate within patient 16, e.g., in a particular pattern. In addition, or instead, processor 40 may generate the notification by transmitting a notification signal to processor 60 of programmer 28 (FIG. 5) via the respective telemetry modules 46, 66. Processor 60 may then control user interface 64 to generate the notification, e.g., via a visible message provided by display 74, via an audible signal, via a somatosensory signal, or any combination thereof.

As discussed above, the notification generated in response to determining the oscillation frequency of bladder 14 is less than or equal to a predetermined threshold value may be presented to patient 16 or a patient caretaker, e.g., to notify patient 16 or the caretaker that the fill level of bladder 14 is elevated, such that voiding is desirable. This notification of an elevated bladder fullness level may be useful if patient 16 is afflicted with a condition in which bladder sensations are reduced or even absent. In addition, if patient 16 is unable to void without assistance (e.g., via catheterization or via assistance in reaching a bathroom), the notification may alert patient 16 or the patient caretaker to the elevated bladder fullness state, such that patient 16 may seek assistance with voiding in a timely manner.

In examples in which a system does not include IMD 22 or programmer 28, such as in the case of system 10, the technique shown in FIG. 7 may be performed by processor 30 of sensor 12, a processor of external device 18, or both. The notification (88) may be provided to patient 16 via sensor 12 (e.g., processor 30 may cause outer housing 38 of sensor 12 (FIG. 3) to vibrate), or via a user interface of external device 18.

Figure 8:
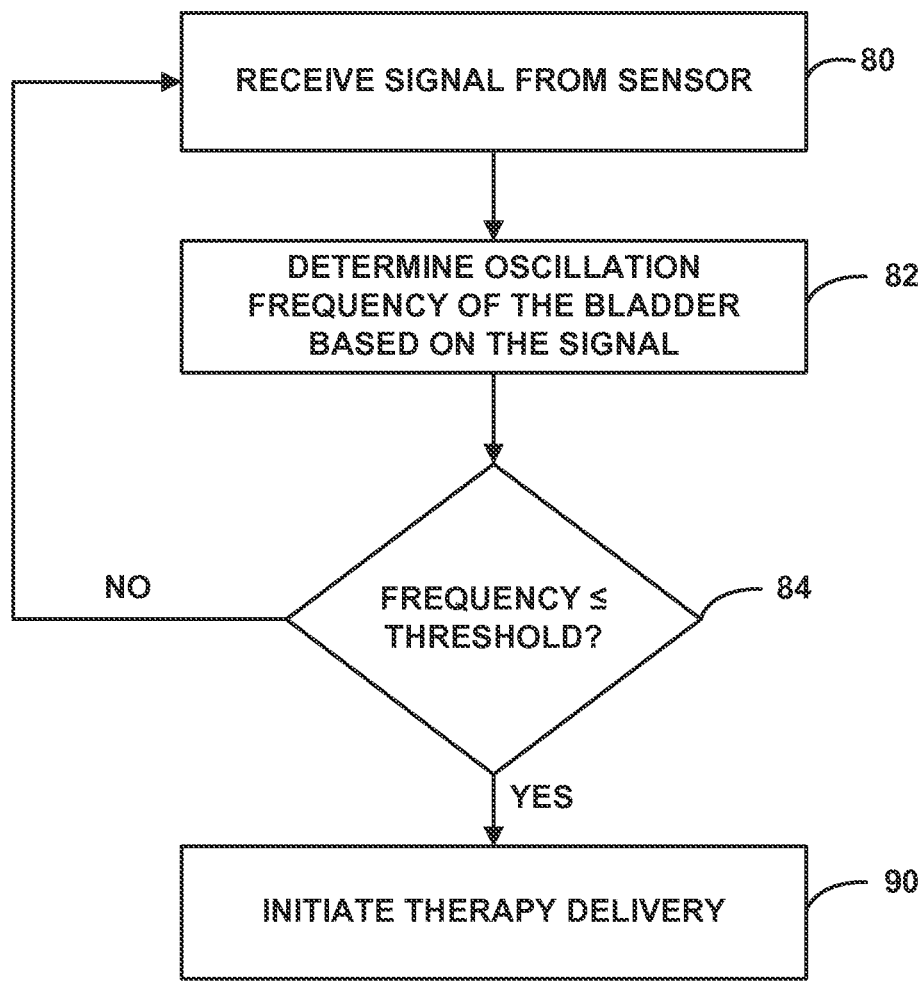
FIG. 8 is a flow diagram of an example technique for initiating therapy delivery to a patient based on an oscillation frequency of a bladder of the patient.

FIG. 8 is a flow diagram of another example of the technique shown in FIG. 6. In the example shown in FIG. 8, after determining the oscillation frequency of bladder 14 is less than or equal to a predetermined threshold value ("YES" branch of block 84), processor 40 controls stimulation generator 42 to initiate delivery of electrical stimulation therapy to patient 16 (90). As discussed above, the electrical stimulation therapy may be configured to help reduce the frequency of micturition bladder contractions, reduce urgency, or otherwise help prevent the occurrence of an involuntary voiding event. The electrical stimulation therapy may be, for example, the first stimulation therapy or the second stimulation therapy described above with respect to FIG. 4. In some examples, prior to initiating therapy delivery (90), stimulation generator 42 may not be actively delivering therapy to patient 16 to manage a lower urinary tract dysfunction of patient 16.

In the technique shown in FIG. 8, system 20 provides closed-loop electrical stimulation therapy to patient 16. In some cases, by implementing the technique shown in FIG. 8, IMD 22 may deliver more efficacious lower urinary tract dysfunction therapy to patient 16 by timing the delivery of stimulation to respond to a specific physiological state (e.g., a particular bladder fullness level) of patient 16.

In other examples of therapy systems, IMD 22 may be configured to provide another type of therapy to patient 16 in addition to or instead of electrical stimulation therapy. For example, IMD 22 may be a drug delivery device that is configured to deliver a pharmaceutical agent to patient 16 that helps manage a lower urinary tract dysfunction of patient 16. The technique shown in FIG. 8 (as well as other techniques described herein, e.g., with respect to FIGS. 9 and 10) may be used with other types of therapy delivery in addition to or instead of electrical stimulation therapy, including drug delivery therapy.

Figure 9:
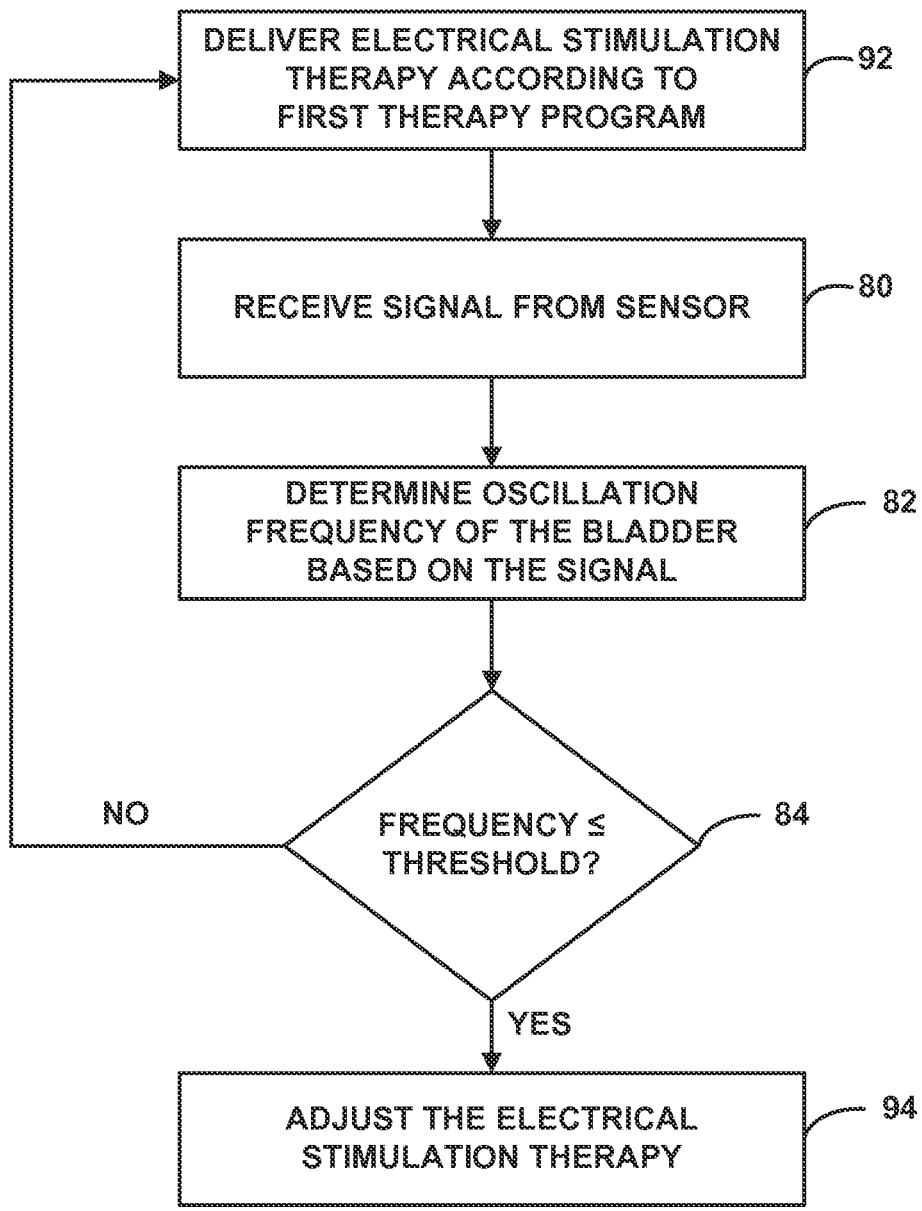
FIG. 9 is a flow diagram of an example technique for adjusting therapy delivery to a patient based on an oscillation frequency of a bladder of the patient.

FIG. 9 is a flow diagram of another example of the technique shown in FIG. 6. In the example shown in FIG. 9, processor 40 controls stimulation generator 42 to generate and deliver electrical stimulation therapy to patient 16 according to a first therapy program, which is configured to help manage lower urinary tract dysfunction (92). The electrical stimulation therapy may be configured to help reduce the frequency of micturition bladder contractions, reduce urgency, promote contraction of the internal urinary sphincter, external urinary sphincter, periurethral muscles or any combination thereof, or otherwise help prevent the occurrence of an involuntary voiding event.

Processor 40 may receive the signal from sensor (80) and determine the frequency of mechanical oscillation of bladder 14 based on the signal (82). In the example shown in FIG. 9, processor 40 determines the frequency of mechanical oscillation of bladder 14 while stimulation generator 42 delivers the electrical stimulation therapy to patient 16. That is, the determined oscillation frequency of bladder 14 is the oscillation frequency that bladder 14 exhibits while patient 16 is receiving the electrical stimulation therapy according to the first therapy programs. In accordance with the technique shown in FIG. 9, in response to determining that the oscillation frequency of bladder 14 is not less than or equal to a predetermined threshold value ("NO" branch of block 84), processor 40 may continue controlling stimulation generator 42 to generate and deliver stimulation therapy to patient 16 according to the first therapy program (92) until the oscillation frequency of bladder 14 is less than or equal to the predetermined threshold value.

In response to determining the oscillation frequency of bladder 14 is less than or equal to a predetermined threshold value ("YES" branch of block 84), processor 40 adjusts the electrical stimulation therapy delivered by stimulation generator 42 (94). In one example, processor 40 adjust at least one stimulation parameter value of the first therapy program, e.g., by modifying the stimulation parameter value or selecting another therapy program from memory 44. Memory 44 may store a plurality of therapy programs and instructions for execution by processor 40 for selecting one of the other therapy programs based on detecting a bladder oscillation frequency that is less than or equal to the threshold value. For example, memory 44 may store instructions that cause processor 40 for selecting a second therapy program from memory 44 in response to determining the oscillation frequency of bladder 14 is less than or equal to a predetermined threshold value. In other examples, memory 44 may store instructions for execution by processor 40 for increasing or decreasing a value of a particular therapy parameter by a particular amount in response to determining the oscillation frequency of bladder 14 is less than or equal to a predetermined threshold value.

Processor 40 may adjust the stimulation therapy (94) in order to, for example, increase an intensity of the stimulation therapy in order to help reduce the increase in urgency and/or the probability that an incontinence event that may be caused by the increase in bladder fullness level indicated by the oscillation frequency that is less than or equal to the threshold value. Thus, in some examples, the first therapy program defines a lower intensity electrical stimulation than the adjusted therapy program. An intensity of stimulation may be a function of, for example, a current or voltage amplitude of the stimulation signal, the frequency of the stimulation signal, the pulse width of the stimulation signal, the shape of the stimulation signal, the duty cycle of the stimulation signal, the electrode combination used to deliver the stimulation signal, or any combination of the stimulation parameters. Thus, in some examples, processor 40 may increase the intensity of stimulation by increasing an amplitude value of the first therapy program or by selecting another therapy program that has a higher amplitude value.

While a relatively high intensity stimulation delivered to patient 16 substantially continuously may be useful for managing urgency and/or urinary incontinence (e.g., reducing or even eliminating the frequency of involuntary voiding events), delivering a relatively low intensity electrical stimulation and increasing the intensity of electrical stimulation in response to oscillation frequency indicative of an elevated bladder fullness level (e.g., in accordance with the technique shown in FIG. 9) may be useful for decreasing power consumption by IMD 22 while still maintaining efficacious stimulation. Additionally, increasing stimulation intensity level in response to a particular physiological condition detected based on the oscillation frequency of bladder 14 may help reduce adaptation of patient 16 to the therapy delivery. "Adaptation" may refer to a phenomenon in which a patient may adapt to stimulation delivered by an IMD over time, such that a certain level of electrical stimulation provided to a tissue site in the patient may be less effective over time.

In some examples, processor 40 may control stimulation generator 42 to switch back to the first therapy program after some event that indicates a lower bladder fullness level, which may indicate the lower intensity therapy may be efficacious for the current patient condition. The event may be, for example, expiration of a predetermined period of time, detection of an oscillation frequency that is greater than the predetermined threshold value or a second threshold value, input from patient 16 or a patient caretaker that indicates patient 16 has voided, or any other suitable indication that the fullness level of bladder 14 has decreased.

FIG. 10 is a flow diagram of another example of the technique shown in FIG. 6. In the example shown in FIG. 10, processor 40 controls stimulation generator 42 to generate and deliver a first electrical stimulation therapy to patient 16 to help manage lower urinary tract dysfunction (96). For example, processor 40 may access memory 44 (FIG. 4) to load a therapy program 50 associated with the first stimulation therapy to stimulation generator 42. Processor 40 may receive the signal from sensor (80) and determine the frequency of the mechanical oscillations of bladder 14 based on the signal (82). In the example shown in FIG. 10, processor 40 determines the frequency of mechanical oscillation of bladder 14 while stimulation generator 42 delivers the first electrical stimulation therapy to patient 16. That is, the determined oscillation frequency of bladder 14 is the oscillation frequency that bladder 14 exhibits while patient 16 is receiving the first electrical stimulation therapy.

Processor 40 compares the determined oscillation frequency to a predetermined threshold value (84). If processor 40 determines that the oscillation frequency of bladder 14 is not less than or equal to a predetermined threshold value ("NO" branch of block 84), processor 40 may continue controlling stimulation generator 42 to generate and deliver the first stimulation therapy to patient 16 (92) until the oscillation frequency of bladder 14 is less than or equal to the predetermined threshold value. In response to determining the oscillation frequency of bladder 14 is less than or equal to a predetermined threshold value ("YES" branch of block 84), processor 40 controls stimulation generator 42 to deliver a second electrical stimulation therapy to patient 16 (98). For example, processor 40 may access memory 44 (FIG. 4) to load a therapy program 50 associated with the second stimulation therapy to stimulation generator 42.

The second stimulation therapy is configured to provide an additional "boost" of therapy over that provided by the first stimulation therapy. The "boost" of therapy may provide short-term boost to the effectiveness of the first stimulation therapy, which may provide an increased protection against the occurrence of involuntary voiding events. For example, the second stimulation therapy may be configured in some examples to elicit a physiological response from patient 16 that is different than the physiological response elicited by the first stimulation therapy. For example, the first stimulation therapy may elicit an afferent response by the patient, whereas the second stimulation therapy may elicit an efferent response. As an example, IMD 22 may deliver the first stimulation therapy to modulate activity of a sacral nerve of patient 16 to elicit an afferent response that relaxes bladder 14, e.g., by minimizing bladder contractions and IMD 22 may deliver the second stimulation therapy to promote contraction of the internal urinary sphincter, external urinary sphincter, periurethral muscles or any combination thereof, which may help prevent the involuntary leakage of urine from bladder 12. In addition, or instead, of the different physiological response, the second stimulation therapy may have a higher intensity than the first stimulation therapy.

The second electrical stimulation therapy may be referred to as a temporary stimulation therapy because the second electrical stimulation therapy is delivered for a predetermined period of time (duration of time), rather than on a regular basis. In addition, in some examples, the second stimulation therapy may be referred to as functional electrical stimulation because the second electrical stimulation therapy elicits movement of muscles of patient 16 that provides a specific functional result. For example, the second stimulation therapy may elicit a contraction of the urinary sphincter of patient 16.

The steps of delivering the first stimulation therapy and determining the oscillation frequency of bladder 14 (82) and comparing the oscillation frequency to a predetermined threshold value (84) are illustrated in FIG. 10 as being sequential, but it should be understood that these steps may be performed simultaneously instead of sequentially.

In some examples, processor 40 controls stimulation generator 42 to deliver only one of the first stimulation therapy or the second stimulation therapy to patient 16 at a time, such that the first stimulation therapy may be suspended while stimulation generator 42 delivers the second stimulation therapy to patient 16 (98). In other examples, processor 40 controls stimulation generator 42 to deliver the first and second stimulation therapies to patient 16 at the same time, e.g., such that the stimulation signals are time interleaved or overlap in time.

In some examples of the technique shown in FIG. 10, the first stimulation therapy may be delivered in as part of open loop therapy that does not use input from a sensor or user to initiate therapy delivery, while the second stimulation therapy is delivered as part of closed-loop therapy that utilizes input from sensor 12 to trigger therapy delivery. In other examples, the first stimulation therapy may also be delivered as part of closed-loop or pseudo closed-loop therapy, e.g., in response to patient input or some sensed physiological parameter. In some examples, stimulation generator 42 delivers the first stimulation therapy (96) chronically, e.g., periodically for an extended period of time, such as hours, days, weeks, to control urinary or fecal incontinence, and the second stimulation therapy is also delivered during this time. In examples in which the first and second stimulation therapies are not delivered simultaneously, stimulation generator 42 delivers the first stimulation therapy until processor 40 detects an oscillation frequency of bladder 14 that triggers delivery of the second stimulation therapy.

In some examples, IMD 22 delivers the second stimulation therapy (98) until the occurrence of some event that indicates a lower bladder fill level, which may indicate only delivering the first stimulation therapy may be efficacious for the current patient condition. The event may be, for example, expiration of a predetermined period of time, detection of an oscillation frequency that is greater than the predetermined threshold value or a second threshold value, input from patient 16 or a patient caretaker that indicates patient 16 has voided, or any other suitable indication that the fullness level of bladder 14 has decreased.

For example, stimulation generator 42 may deliver the second stimulation therapy for a predetermined period of time, e.g., about 10 seconds to about 50 seconds, which may be stored by memory 44 of IMD 22 or a memory of another device, such as sensor 12 or programmer 28. The duration of the predetermined period of time may be selected such that an imminent involuntary voiding event is suppressed. In one example, after expiration of the predetermined period of time, processor 40 controls stimulation generator 42 to stop delivering of the second stimulation therapy and deliver the first electrical stimulation therapy (96).

In other examples, rather than automatically reverting back to the first stimulation therapy after expiration of the predetermined period of time, processor 40 may determine whether a bladder fullness level of patient 16 is still elevated. For example, after the predetermined period of time has passed, processor 40 may again determine an oscillation frequency of the bladder based on a signal received from sensor 12. For ease of description, the oscillation frequency determined after the predetermined period of time may be referred to as a "second" oscillation frequency. Processor 40 may compare the second oscillation frequency to the predetermined threshold value and, if the second oscillation frequency is less than or equal to the predetermined threshold value, processor 40 may determine that the bladder fullness level is still high enough to merit delivery of the second stimulation therapy. Thus, processor 40 may continue controlling stimulation generator 42 to generate and deliver the second stimulation therapy to patient 16 for another predetermined period of time. Processor may continue this process until the second oscillation frequency is greater than the predetermined threshold value, at which point, processor 40 may determine that the bladder fill level of patient 16 has decreased, such that the second stimulation therapy may no longer be necessary to provide efficacious therapy. Thus, processor 40 may control stimulation generator 42 to terminate delivery of the second stimulation therapy and deliver the first stimulation therapy to patient 16.

In other examples, IMD 22 delivers the second stimulation therapy for a period of time controlled by patient 16. For example, patient 16 may control the duration of the second stimulation therapy by interacting with programmer 28, e.g., by interacting with user interface 64 (FIG. 5) to provide input indicating the second stimulation therapy should be terminated, that patient 16 has voided, or another indication that the second stimulation therapy is no longer desired. Processor 60 of programmer 28 (FIG. 5) may transmit a signal indicative of the patient input to processor 40 of IMD 22 via the respective telemetry modules 66, 46.

After completion of the delivery of the second stimulation therapy, IMD 22 reverts back to delivering the first stimulation therapy (98) and the technique shown in FIG. 10 may continue. In accordance with the technique shown in FIG. 10, IMD 22 delivers the first stimulation therapy and, when triggered, delivers the second stimulation therapy for a limited duration of time (e.g., shorter in duration than the duration of time that the first stimulation therapy is delivered). That is, IMD 22 delivers chronic stimulation for an extended period of time via the first stimulation therapy, and, when the oscillation frequency indicates an elevated bladder fill level, delivers an additional boost of stimulation via the second stimulation therapy. The boost of stimulation is provided for a comparatively short period of time within the extended period of time during which the chronic therapy delivery is provided.

By implementing the technique shown in FIG. 10, IMD 22 may provide responsive stimulation to control urinary incontinence. Delivering the second stimulation therapy upon detection of an oscillation frequency less than or equal to the predetermined threshold value, rather than on a substantially regular basis, may help reduce muscle fatigue by limiting the amount of the second stimulation therapy provided to patient 16. In addition, implementing the second stimulation therapy only when the elevated bladder fill level is detected may help conserve power of power source 60 of IMD 22. Conserving power may help elongate the useful life of IMD 22.

In some examples, IMD 22 delivers the first and second stimulation therapies according to different sets of stimulation parameters and/or to different target tissue sites within the patient. However, in some examples, the first and second stimulation therapies are delivered to the same nerve (e.g., the sacral or pudendal nerve). In some examples, IMD 22 may deliver the first stimulation therapy to a sacral nerve to improve pelvic floor muscle tone or to an afferent fiber of the sacral or pudendal nerves to inhibit bladder contractions, e.g., to relax the bladder. In addition, in some examples, the first stimulation therapy helps close or maintain internal urinary sphincter closure or urethral tone. IMD 22 may deliver the second stimulation therapy to a hypogastric nerve, a pudendal nerve, a dorsal penile nerve in a male patient, a dorsal clitoral nerve in a female patient, or to the external urinary sphincter or any combination thereof to promote contraction of the internal urinary sphincter, or promote external urinary sphincter closure or periurethral muscle contraction.

In other examples of the techniques described herein, including the techniques described with respect to FIGS. 6-10, processor 40 may compare the determined oscillation frequency of bladder 14 to a plurality of threshold values and take a responsive action based on the comparison. For example, processor 40 may determine if the determined oscillation frequency is less than or equal to a first threshold value, and, if so, determine whether the determined oscillation frequency is less than or equal to a second threshold value. The first threshold value may be greater than the second threshold value. This may be repeated for any suitable number of progressively decreasing threshold values. Each of the threshold values may be associated with a respective responsive action. If the determined oscillation frequency is not less than or equal to the first threshold value, processor 40 may take no responsive action. If the determined oscillation frequency is less than or equal to the first threshold value and is not less than or equal to the second threshold value, processor 40 may take the responsive action associated with the first threshold value. If the determined oscillation frequency is less than or equal to the first threshold value and the second threshold value, processor 40 may take the responsive action associated with the second threshold value.

In other examples of the techniques described herein, including the techniques described with respect to FIGS. 6-10, rather than comparing the determined oscillation frequency of bladder 14 to a threshold value (84), processor 40 of IMD 22 (or a processor of another device, such as sensor 12 or programmer 28) may take a responsive action based on the determined (e.g., sensed) oscillation frequency using another technique. For example, processor 40 (or another processor) may use a linear or non-linear function to control electrical stimulation delivered by IMD 22 based on the oscillation frequency. As an example, processor 40 may periodically adjust a stored electrical stimulation parameter value (e.g., amplitude), e.g., currently implemented by stimulation generator 42, based on the determined oscillation frequency by referencing information that establishes a relationship between oscillation frequency of bladder 14 and the electrical stimulation parameter value. There may be, for example, an inverse relationship between the amplitude of electrical stimulation signals delivered by IMD 22 and the sensed oscillation frequency.

The predetermined relationship between oscillation frequency of bladder 14 and the electrical stimulation parameter value applied by processor 40 to take a responsive action (86) may be determined using any suitable function, such as a linear or non-linear function. In some examples, memory 44 of IMD 22 or another device (e.g., sensor 12 or programmer 28) may store a data structure that associates a plurality of oscillation frequency values with a respective electrical parameter value. At least two stored oscillation frequency values are associated with different electrical stimulation parameter values. The predetermined relationship may be selected such that as the bladder fullness level, as indicated by the oscillation frequency decreases, the intensity of electrical stimulation increases. In these examples, after determining the oscillation frequency of bladder (82), processor 40 (or another processor) may take a responsive action based on the determined oscillation frequency by determining the stimulation parameter value associated with the determined oscillation frequency in memory 44 and controlling stimulation generator 42 to generate and deliver electrical stimulation to patient 16 in accordance with the determined stimulation parameter value.

A similar technique may be used to control the timing of any suitable responsive action based on a detected oscillation frequency value, and not just the adjustment to therapy delivery described above. In some examples, processor 40 of IMD 22 or a processor of another device may periodically determine the oscillation frequency, e.g., based on the most recent data sensed by sensor 12 (82), and then determine what action should be taken based on the determined oscillation frequency. Memory 44 of IMD 22 or a memory of another device may associate different oscillation frequency values (e.g., discrete values or a plurality of ranges of values) with different responsive actions, and processor 40 may reference this information to determine what responsive action to take based on detected oscillation frequency of bladder 14. Processor 40 may then determine the responsive action to take to be the responsive action associated with the detected oscillation frequency of bladder 14 in memory 44 (or a memory of another device).

This technique for taking a responsive action based on a determined oscillation frequency of bladder 14 may be implemented by processor 40 of IMD 22 (or one or more processors of one or more other devices) to provide a more continuous or adaptive therapy to patient 16 compared to the technique described above in which the responsive action is taken based on a more discrete event (e.g., the detection of an oscillation frequency less than or equal to a predetermined threshold value).

In some cases, bladder 14 may not be mechanically oscillating, e.g., because the oscillations have stopped since the last non-micturition contraction. In these cases, the current bladder fullness level may be determined using past determined mechanical oscillation frequencies. As discussed above, in some examples, a current bladder fill level (e.g., bladder volume) of patient 16 may be predicted based on a function that indicates the rate of change of volume of bladder 14, where the function is based on a plurality of bladder oscillation frequencies. In some examples, a fading set of change in volume (as indicated by bladder oscillation frequencies) per change in time ($\Delta V/\Delta t$) measurements may be used to determine the rate of change of volume (e.g., the rate of change of bladder oscillation frequencies) of bladder 14 at various points in time (e.g., relative to the start of a micturition cycle). Periodically, processor 40 (or another processor) may determine a bladder oscillation frequency and update the volume prediction function, which may make the volume prediction function more accurate. In some examples, processor 40 (or another processor) may determine the current fullness level (e.g., also referred to as the current bladder volume) of bladder 14 by determining the point in time, e.g., in the micturition cycle of the patient 16, and determining the bladder fullness level based on amount of time that has elapsed since the beginning of the micturition cycle (e.g., since the last voiding event) or another known bladder fill level and the function that indicates the change in volume per unit time. For example, processor 40 may predict the current oscillation frequency of bladder 14 based on the function (as opposed to based on a currently sensed oscillation frequency); the predicted oscillation frequency may indicate the relative bladder volume.

In some examples, the measured bladder volume with the time since the last voiding event (also referred to as a micturition event) may be used (e.g., by processor 40 or another processor) to measure urine rate. Bladder volume and urine rate may then be used to produce a bladder volume function that would predict bladder volume between bladder oscillation frequency measurements.

In some examples, any of the responsive actions described above may then be taken based on a predicted bladder fullness level (also referred to herein as a current bladder fullness level) of patient 16 determined using the function that indicates the change in volume of bladder 14 over time. For example, memory 44 of IMD 22 or a memory of another device may associate a plurality of bladder fullness levels of patient 16 with respective responsive actions, as discussed above. As another examples, processor 40 may take a responsive action in response to determining the current bladder fullness level is greater than or equal to a predetermined threshold value, which may be stored by memory 44 of IMD 22 or a memory of another device.

In one example, the disclosure is directed to a system comprising a sensor configured to generate a signal indicative of mechanical oscillation of a bladder of a patient, and a processor configured to receive the signal from the sensor, determine an oscillation frequency of the bladder based on the signal, determine, based on the oscillation frequency of the bladder, the urine volume within the bladder (also referred to herein as bladder volume).

In another example, the disclosure is directed to a system comprising a sensor configured to generate a signal indicative of mechanical oscillation of a bladder of a patient, and a processor configured to receive the signal from the sensor, determine an oscillation frequency of the bladder based on the signal, determine, based on the oscillation frequency of the bladder, the urine volume within the bladder. Additionally, recorded times with urine volumes within the bladder since micturition may be used to assess rate of urine production. Temporal rates of urine production along with urine volumes within the bladder can be used to produce a urine volume within the bladder or a bladder volume function in time. This function may be applied, e.g., by a processor (e.g., processor 40 of IMD 22 or a processor of another device) to determine a current bladder volume between mechanical oscillation measurement events.

In another example, the disclosure is directed to a method comprising with a processor, receiving, from a sensor, a signal indicative of mechanical oscillations of a bladder of a patient, with the processor, determining an oscillation frequency of the bladder based on the signal, with the processor, determining, based on the oscillation frequency of the bladder, and a history of the measured oscillation frequencies, a function that indicates bladder volume. Computed bladder volume may be used to take a responsive action based on the current bladder volume, e.g., as described above.

In another example, the disclosure is directed to a system comprising means for receiving, from a sensor, a signal indicative of mechanical oscillations of a bladder of a patient, means for determining an oscillation frequency of the bladder based on the signal, means for determining, based on the oscillation frequency of the bladder, and a history of the measured oscillation frequencies, a function that indicates bladder volume can be generated. The system comprises means for computing the bladder volume and means for taking a responsive action based on the current bladder volume.

In another example, the disclosure is directed to a computer-readable medium comprising instructions. When executed by a processor, the instructions cause the processor to receive, from a sensor, a signal indicative of mechanical oscillations of a bladder of a patient, determine an oscillation frequency of the bladder based on the signal, determine, based on the oscillation frequency of the bladder, and a history of the measured oscillation frequencies, a function that computes bladder volume, and determine a current bladder volume based on the function, and take a responsive action based on the current bladder volume.

The techniques described in this disclosure, including those attributed to sensor 12, external device 18, IMD 22, programmer 28, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. While the techniques described herein are primarily described as being performed by processor 30 of sensor 12, processor 40 of IMD 22, and/or processor 60 of programmer 28, any one or more parts of the techniques described herein may be implemented by a processor of one of sensor 12, external device 18, IMD 22, programmer 28, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. A system comprising:
   a sensor configured to generate a signal indicative of an oscillation frequency of mechanical oscillation of a bladder of a patient; and
   a processor configured to receive the signal from the sensor,
   determine, based on the signal, that the oscillation frequency of the bladder is less than or equal to a threshold value, and
   responsive to determining that the oscillation frequency of the bladder is less than or equal to the threshold value, take a responsive action, whereby the threshold value is indicative of a bladder fullness level.

2. The system of claim 1, further comprising a memory that associates a plurality of oscillation frequencies with respective responsive actions, wherein the processor is configured to determine the responsive action associated with the oscillation frequency in the memory.

3. The system of claim 1, further comprising a medical device configured to deliver therapy to the patient, wherein the processor is configured to take the responsive action by at least controlling the medical device to initiate therapy delivery to the patient.

4. The system of claim 3, wherein the oscillation frequency comprises a first oscillation frequency, and wherein the processor is configured to, subsequent to controlling the medical device to initiate therapy delivery, determine a second oscillation frequency of the bladder based on the signal, and control the medical device to at least one of terminate, or adjust the delivery of therapy to the patient based on the second oscillation frequency.

5. The system of claim 1, further comprising a medical device configured to deliver therapy to the patient, wherein the processor is configured to take the responsive action by at least controlling the medical device to adjust at least one parameter of therapy delivered to the patient at the time the processor determined that the oscillation frequency of the bladder is less than or equal to the threshold value.

6. The system of claim 5, wherein the medical device is configured to deliver electrical stimulation therapy to the patient according to a set of therapy parameter values, and the processor is configured to control the medical device to adjust at least one parameter of therapy by at least controlling the medical device to adjust at least one electrical stimulation parameter value of the set of therapy parameter values.

7. The system of claim 1, further comprising a medical device, wherein the medical device is configured to deliver a first electrical stimulation therapy to the patient to generate a first physiological effect, wherein the processor is configured to determine the oscillation frequency while the medical device is delivering the first electrical stimulation therapy to the patient, and wherein the processor is configured to take the responsive action by at least controlling the medical device to deliver a second electrical stimulation therapy to the patient, wherein the delivery of the second electrical stimulation therapy generates a second physiological effect that is different than the first physiological effect.

8. The system of claim 7, wherein the first physiological effect comprises inhibiting contraction of the bladder of the patient, and the second physiological effect comprises promoting contraction of one or more of a bladder outlet of the patient, an internal urinary sphincter of the patient, an external urinary sphincter of the patient, or periurethral muscles of the patient.

9. The system of claim 1, wherein the processor is configured to take the responsive action by at least generating a notification that indicates an elevated bladder fullness level.

10. The system of claim 1, wherein the sensor comprises at least one of an acoustic or pressure sensor, a flexible printed circuit comprising pressure sensitive ink, a piezoresistor, a piezoelectric crystal, a capacitive sensor, a load cell, a force sensor, or a displacement sensor.

11. A method comprising:
    with a processor, receiving, from a sensor configured to generate a signal indicative of an oscillation frequency of mechanical oscillations of a bladder of a patient, the signal;
    with the processor, determining, based on the signal, that the oscillation frequency of the bladder is less than or equal to a threshold value; and
    with the processor, responsive to determining that the oscillation frequency of the bladder is less than or equal to the threshold value, taking a responsive action, whereby the threshold value is indicative of a bladder fullness level.

12. The method of claim 11, further comprising, with the processor, determining the responsive action to take by at least determining the responsive action associated with the oscillation frequency in a memory, wherein the memory associates a plurality of oscillation frequencies with respective responsive actions.

13. The method of claim 11, wherein taking the responsive action based on the oscillation frequency comprises, with the processor, controlling a medical device to initiate therapy delivery to the patient.

14. The method of claim 13, wherein the oscillation frequency comprises a first oscillation frequency, and the method further comprises:
    subsequent to controlling the medical device to initiate therapy delivery, determining, with the processor, a second oscillation frequency of the bladder based on the signal; and
    controlling the medical device to at least one of terminate or adjust the delivery of therapy to the patient based on the second oscillation frequency.

15. The method of claim 11, wherein taking the responsive action based on the bladder contraction frequency comprises, with the processor, controlling a medical device to adjust at least one parameter of therapy delivered to the patient at the time the sensor generated a portion of the signal on which the oscillation frequency was determined to be less than or equal to the threshold value.

16. The method of claim 15, wherein the medical device is configured to deliver electrical stimulation therapy to the patient according to a set of therapy parameter values, and controlling the medical device to adjust at least one parameter of therapy comprises controlling the medical device to adjust at least one electrical stimulation parameter value of the set of therapy parameter values.

17. The method of claim 11, further comprising controlling a medical device to deliver a first electrical stimulation therapy to the patient to generate a first physiological effect, wherein determining that the oscillation frequency is less than or equal to a threshold value comprises determining that the oscillation frequency is less than or equal to a threshold value while the medical device is delivering the first electrical stimulation therapy to the patient, and wherein taking the responsive action comprises, with the processor, controlling the medical device to deliver a second electrical stimulation therapy to the patient, wherein the delivery of the second electrical stimulation therapy generates a second physiological effect that is different than the first physiological effect.

18. The method of claim 17, wherein the first physiological effect comprises inhibiting contraction of the bladder of the patient, and the second physiological effect comprises promoting contraction of one or more of a bladder outlet of the patient, an internal urinary sphincter of the patient, an external urinary sphincter of the patient, or periurethral muscles of the patient.

19. The method of claim 11, wherein taking the responsive action comprises generating a notification that indicates an elevated bladder fullness level.

20. The method of claim 11, wherein the sensor comprises at least one of an acoustic or a pressure sensor, a flexible printed circuit comprising pressure sensitive ink, a piezoresistor, a piezoelectric crystal, a capacitive sensor, a load cell, a force sensor, or a displacement sensor.

21. A system comprising:
means for receiving, from a sensor, a signal indicative of an oscillation frequency of mechanical oscillations of a bladder of a patient;
means for determining, based on the signal, that the oscillation frequency of the bladder is less than or equal to a threshold value; and
means for, responsive to determining that the oscillation frequency of the bladder is less than or equal to the threshold value, taking a responsive action, whereby the threshold value is indicative of a bladder fullness level.

22. The system of claim 21, further comprising:
means for storing a plurality of oscillation frequencies and respective responsive actions; and
means for determining the responsive action, wherein the means for determining the responsive action is configured to determine the responsive action associated with the oscillation frequency in the means for storing.

23. The system of claim 21, further comprising means for delivering therapy to the patient, wherein the means for taking the responsive action controls the means for delivering therapy to the patient based on the oscillation frequency.

24. The system of claim 21, further comprising means for generating a notification, wherein the means for taking the responsive action controls the means for generating a notification to generate a notification based on the oscillation frequency.

25. A computer-readable medium comprising instructions that, when executed by a processor, cause the processor to:
receive, from a sensor, a signal indicative of an oscillation frequency of mechanical oscillations of a bladder of a patient;
determine, based on the signal, that the oscillation frequency of the bladder is less than or equal to a threshold value; and
responsive to determining that the oscillation frequency of the bladder is less than or equal to the threshold value, take a responsive action, whereby the threshold value is indicative of a bladder fullness level.

26. The computer-readable medium of claim 25, wherein the instructions cause the processor to determine the responsive action to take by at least accessing a memory that associates a plurality of oscillation frequencies with respective responsive actions and determining the responsive action associated with the oscillation frequency in the memory.

27. The computer-readable medium of claim 25, wherein the instructions cause the processor to take the responsive action by controlling therapy delivery by a medical device.

28. The computer-readable medium of claim 25, wherein the instructions cause the processor to take the responsive action by generating a notification indicative of an elevated bladder fullness level.

29. A system comprising:
a sensor configured to generate a signal indicative of an oscillation frequency of mechanical oscillation of a bladder of a patient; and
a processor configured to receive the signal from the sensor, determine a change in the oscillation frequency of the bladder based on the signal, determine, based on the change in the oscillation frequency of the bladder, a function that indicates a change in volume of the bladder of the patient per unit time, and determine a current bladder volume based on the function, whereby a decrease in oscillation frequency is indicative of an increase in the volume of the bladder.

30. The system of claim 29, wherein the processor is configured to determine the current bladder volume based on the function by at least determining an amount of time that has elapsed since a last voiding event, and determining a total change in volume of the bladder since the last voiding event based on the function and the amount of time that has elapsed since the last voiding event.

31. The system of claim 29, wherein the processor is configured to take a responsive action based on the current bladder volume.

32. The system of claim 31, wherein the processor is configured to compare the current bladder volume to a threshold value, and take the responsive action in response to determining the current bladder volume is greater than or equal to the threshold value.

33. The system of claim 31, further comprising a memory that associates a plurality of bladder volumes with respective responsive actions, wherein the processor is configured to determine the responsive action associated with the current bladder volume in the memory.

34. The system of claim 31, further comprising a medical device configured to deliver therapy to the patient, wherein the processor is configured to take the responsive action by at least controlling the medical device to initiate therapy delivery to the patient.

35. The system of claim 34, wherein the oscillation frequency comprises a first oscillation frequency, and wherein the processor is configured to, subsequent to controlling the medical device to initiate therapy delivery, determine an updated bladder volume based on the function and an amount of time that has elapsed since the last voiding event, and control the medical device to at least one of terminate, or adjust the delivery of therapy to the patient based on the updated bladder volume.

36. The system of claim 31, further comprising a medical device configured to deliver therapy to the patient, wherein the processor is configured to take the responsive action by at least controlling the medical device to adjust at least one parameter of therapy delivered to the patient at the time the processor determined the current bladder volume.

37. The system of claim 36, wherein the medical device is configured to deliver electrical stimulation therapy to the patient according to a set of therapy parameter values, and the processor is configured to control the medical device to adjust at least one parameter of therapy by at least controlling the medical device to adjust at least one electrical stimulation parameter value of the set of therapy parameter values.

38. The system of claim 31, further comprising a medical device, wherein the medical device is configured to deliver a first electrical stimulation therapy to the patient to generate a first physiological effect, wherein the processor is configured to determine the current bladder volume while the medical device is delivering the first electrical stimulation therapy to the patient, and wherein the processor is configured to take the responsive action by at least controlling the medical device to deliver a second electrical stimulation therapy to the patient, wherein the delivery of the second electrical stimulation therapy generates a second physiological effect that is different than the first physiological effect.

39. The system of claim 38, wherein the first physiological effect comprises inhibiting contraction of the bladder of the patient, and the second physiological effect comprises promoting contraction of one or more of a bladder outlet of the patient, an internal urinary sphincter of the patient, an external urinary sphincter of the patient, or periurethral muscles of the patient.

40. The system of claim 31, wherein the processor is configured to take the responsive action by at least generating a notification that indicates an elevated bladder fullness level.

41. The system of claim 29, wherein the sensor comprises at least one of an acoustic or pressure sensor, a flexible printed circuit comprising pressure sensitive ink, a piezoresistor, a piezoelectric crystal, a capacitive sensor, a load cell, a force sensor, or a displacement sensor.

42. A method comprising:
   with a processor, receiving, from a sensor, a signal indicative of an oscillation frequency of mechanical oscillations of a bladder of a patient;
   with the processor, determining a change in the oscillation frequency of the bladder based on the signal;
   with the processor, determining, based on the change in the oscillation frequency of the bladder, a function that indicates a change in volume of the bladder of the patient per unit time;
   with the processor, determining a current bladder volume based on the function, whereby a decrease in oscillation frequency is indicative of an increase in the volume of the bladder; and
   with the processor, taking a responsive action based on the current bladder volume.

43. The method of claim 42, wherein determining the current bladder volume comprises:
   determining an amount of time that has elapsed since a last voiding event; and
   determining a total change in volume of the bladder since the last voiding event based on the function and the amount of time that has elapsed since the last voiding event.

44. The method of claim 42, wherein taking the responsive action comprises:
   with the processor, comparing the current bladder volume to a threshold value; and
   with the processor, taking the responsive action in response to determining the current bladder volume is greater than or equal to the threshold value.

45. The method of claim 42, further comprising, with the processor, determining the responsive action to take by at least determining the responsive action associated with the current bladder volume in a memory, wherein the memory associates a plurality of bladder volumes with respective responsive actions.

46. The method of claim 42, wherein taking the responsive action based on the current bladder volume comprises, with the processor, controlling a medical device to initiate therapy delivery to the patient.

47. The method of claim 46, wherein the oscillation frequency comprises a first oscillation frequency, and the method further comprises:
   subsequent to controlling the medical device to initiate therapy delivery, determining, with the processor, an updated bladder volume of the patient based on the function and the amount of time that has elapsed since the last voiding event: and
   controlling the medical device to at least one of terminate or adjust the delivery of therapy to the patient based on the updated bladder volume.

48. The method of claim 42, wherein taking the responsive action based on the current bladder volume comprises, with the processor, controlling a medical device to adjust at least one parameter of therapy delivered to the patient at the time the current bladder volume was determined.

49. The method of claim 48, wherein the medical device is configured to deliver electrical stimulation therapy to the patient according to a set of therapy parameter values, and controlling the medical device to adjust at least one parameter of therapy comprises controlling the medical device to adjust at least one electrical stimulation parameter value of the set of therapy parameter values.

50. The method of claim 42, further comprising controlling a medical device to deliver a first electrical stimulation therapy to the patient to generate a first physiological effect, wherein determining the current bladder volume comprises determining the current bladder volume while the medical device is delivering the first electrical stimulation therapy to the patient, and wherein taking the responsive action comprises, with the processor, controlling the medical device to deliver a second electrical stimulation therapy to the patient, wherein the delivery of the second electrical stimulation therapy generates a second physiological effect that is different than the first physiological effect.

51. The method of claim 50, wherein the first physiological effect comprises inhibiting contraction of the bladder of the patient, and the second physiological effect comprises promoting contraction of one or more of a bladder outlet of the patient, an internal urinary sphincter of the patient, an external urinary sphincter of the patient, or periurethral muscles of the patient.

52. The method of claim 42, wherein taking the responsive action comprises generating a notification that indicates an elevated bladder fullness level.

53. The method of claim 42, wherein the sensor comprises at least one of an acoustic or pressure sensor, a flexible printed circuit comprising pressure sensitive ink, a piezoresistor, a piezoelectric crystal, a capacitive sensor, a load cell, a force sensor, or a displacement sensor.

54. A system comprising:
   means for receiving, from a sensor, a signal indicative of an oscillation frequency of mechanical oscillations of a bladder of a patient;
   means for determining a change in the oscillation frequency of the bladder based on the signal;
   means tor determining, based on the change in the oscillation frequency of the bladder, a function that indicates a change in volume of the bladder of the patient per unit time;

means tor determining a current bladder volume based on the function; and means for taking a responsive action based on the current bladder volume, whereby a decrease in oscillation frequency is indicative of an increase in the volume of the bladder.

55. The system of claim 54, wherein the means for determining the current bladder volume comprises:

means for determining an amount of time that has elapsed since a last voiding event; and means for determining a total change in volume of the bladder since the last voiding event based on the function and the amount of time that has elapsed since the last voiding event.

56. The system of claim 54, wherein the means for taking the responsive action compares the current bladder volume to a threshold value and takes the responsive action in response to determining the current bladder volume is greater than or equal to the threshold value.

57. The system of claim 54, further comprising:

means for storing a plurality of bladder volumes and respective responsive actions; and means for determining the responsive action, wherein the means for determining the responsive action is configured to determine the responsive action associated with the current bladder volume in the means for storing.

58. The system of claim 54, further comprising means for delivering therapy to the patient, wherein the means for taking the responsive action controls the means for delivering therapy to the patient based on the current bladder volume.

59. The system of claim 54, further comprising means for generating a notification, wherein the means for taking the responsive action controls the means for generating a notification to generate a notification based on the current bladder volume.

60. A computer-readable medium comprising instructions that, when executed by a processor, cause the processor to:

receive, from a sensor, a signal indicative of an oscillation frequency of mechanical oscillations of a bladder of a patient;

determine a change in the oscillation frequency of the bladder based on the signal;

determine, based on the change in the oscillation frequency of the bladder, a function that indicates a change in volume of the bladder of the patient per unit time;

determine a current bladder volume based on the function, whereby a decrease in oscillation frequency is indicative of an increase in the volume of the bladder; and take a responsive action based on the current bladder volume.

61. The computer-readable medium of claim 60, wherein the instructions cause the processor to determine the current bladder volume by at least by at least determining an amount of time that has elapsed since a last voiding event, and determining a total change in volume of the bladder since the last voiding event based on the function and the amount of time that has elapsed since the last voiding event.

62. The computer-readable medium of claim 60, wherein the instructions cause the processor to compare the current bladder volume to a threshold value and takes the responsive action in response to determining the current bladder volume is greater than or equal to the threshold value.

63. The computer-readable medium of claim 60, wherein the instructions cause the processor to determine the responsive action to take by at least accessing a memory that associates a plurality of bladder volumes with respective responsive actions and determining the responsive action associated with the current bladder volume in the memory.

64. The computer-readable medium of claim 60, wherein the instructions cause the processor to take the responsive action by controlling therapy delivery by a medical device.

65. The computer-readable medium of claim 60, wherein the instructions cause the processor to take the responsive action by generating a notification indicative of an elevated bladder fullness level.

* * * * *